United States Patent [19]
Hughes et al.

[11] Patent Number: 5,557,103
[45] Date of Patent: Sep. 17, 1996

[54] METHOD OF ANALYZING DRILLING FLUIDS

[75] Inventors: Trevor L. Hughes, Cherry Hinton; Hemant K. J. Ladva, Cambridge; Peter V. Coveney, Epping, all of England

[73] Assignee: Dowell, a division of Schlumberger Technology Corp., Houston, Tex.

[21] Appl. No.: 355,796

[22] Filed: Dec. 14, 1994

[30] Foreign Application Priority Data

Dec. 17, 1993 [GB] United Kingdom ............... 9325885

[51] Int. Cl.6 .................. G01N 21/35; G01N 33/24
[52] U.S. Cl. ............... 250/255; 250/256; 250/339.12
[58] Field of Search ............... 250/255, 339.07, 250/339.08, 339.12, 340, 256

[56] References Cited

U.S. PATENT DOCUMENTS

| | | | |
|---|---|---|---|
| 4,878,382 | 11/1989 | Jones et al. | 73/153 |
| 5,161,409 | 11/1992 | Hughes et al. | 250/255 |
| 5,306,909 | 4/1994 | Jones et al. | 250/255 |
| 5,360,738 | 11/1994 | Jones et al. | 250/255 X |

Primary Examiner—Carolyn E. Fields
Assistant Examiner—Edward J. Glick
Attorney, Agent, or Firm—John E. Vick, Jr.

[57] ABSTRACT

A method of quantitative analysis of free organic components in a drilling fluid comprising separating solid and liquid components of the drilling fluid using a non-filtering technique such as centrifuging, mixing a sample of the liquid components with a solution of an inorganic carrier such as 2M KBr and analyzing the mixture using infrared spectroscopy so as to determine the amount of organic components in the mixture and deriving the amount of free organic components in the drilling fluid from this analysis. In one embodiment, the mixture is dried to leave a solid mixture of the organic components and the carrier. In this case, the sample is preferably analyzed using a reflectance technique such as diffuse reflectance infrared spectroscopy. In another embodiment, the mixture is analyzed as a liquid, preferably using a direct transmission technique. In both the liquid and solid cases, Fourier transform infrared spectroscopy is preferred.

7 Claims, 34 Drawing Sheets

METHOD OF ANALYZING DRILLING FLUIDS

FIELD OF THE INVENTION

The present invention relates to a method of analysing drilling fluids, and concerns in particular the analysis of water-based drilling fluids containing organic components such as polymers.

BACKGROUND OF THE INVENTION

In order to optimise the performance of a drilling fluid during a drilling operation the physical and chemical properties of the fluid must be carefully controlled. The rheological properties—viscosity, yield stress and gel strength—of the fluid are of particular importance because they are related to the removal of drilled rock cuttings from the borehole, the holding of rock cuttings and weighting agents in suspension during periods of no circulation, and the removal of rock cuttings and drilled solids by surface solids control equipment. The fluid loss properties of the fluid result in the formation of a filter-cake on permeable rock sections of the wellbore so as to minimise losses of the continuous phase of the fluid to the formation during drilling. Thus, both rheological and fluid loss properties of the drilling fluid combine to prevent an accumulation of drilled solids within the circulating fluid, and so result in an optimum drilling rate of penetration.

A wide variety of organic and polymer additives have found extensive use in water-based drilling fluids, examples of which can be found in Chilingarian, G. V. and Vorabutr, P., "Drilling and drilling fluids", Elsevier Science Publishers B. V. (1983), Gray, G. R. and Darley, H. C. H., "Composition and properties of oil well drilling fluids", Gulf Publishing Company (1981) and "1992–93 Environmental Drilling and Completion Fluids Directory", *Offshore/Oilman,* September 1992. These additives are used to formulate a fluid with the required viscosity, yield stress, gel strength and fluid loss properties for a particular drilling application. An additional and increasingly important function of organic and polymer additives used in water-based drilling fluids is the stabilisation of water-sensitive rock formations such as shales. Wellbore stabilisation is achieved both by interactions between additives and the wellbore wall to prevent swelling, dispersion and subsequent erosion of shales, and by interactions with drilled cuttings to prevent cuttings dispersion so as to achieve optimum removal of drilled material by surface solids control equipment.

The current standard procedure for field-testing drilling fluids is given in the American Petroleum Institute (API) "Recommended Practice Standard Procedure for Field Testing Drilling Fluids", RP 13B, 12th ed., September 1988. The document defines field procedures for determining both the physical and chemical properties of water-based and oil-based drilling fluids. The API methods for chemical analysis of water-based drilling fluids include determinations of pH, alkalinity and lime content, chloride, calcium, magnesium, calcium sulphate, formaldehyde, sulphide, carbonate and potassium; they do not, though, include any methods for determining the concentration of organic and polymer additives in water-based drilling fluids. However, there are a number of other oilfield publications which have proposed methods for determining certain polymers in drilling fluids.

For example, there are several published methods which are proposed for quantifying the polymer, partially hydrolysed polyacrylamide (PHPA), in drilling fluids. Fraser, L. J., "New method accurately analyzes PHPA's in muds", *Oil & Gas Journal,* July 1987 proposes a procedure which involves (i) alkaline hydrolysis of a whole mud or mud filtrate sample, (ii) complexation of the ammonia released using a boric acid absorbing solution, and (iii) titration with a standard acid solution. McCulley, L. Z. and Malachosky, E., "A new method for the quantitative determination of the PHPA polymer content of drilling fluids and other aqueous systems", SPE 22580, presented at the 66th Annual Technical Conference & Exhibition, Dallas, October 1991, reviews methods based on an alkaline hydrolysis of the sample, noting that even the vigorous reaction conditions used by Fraser may not be adequate to effect complete conversion due to shielding of the amide groups in the high molecular weight PHPA chain; they also raise an objection to the use of mud filtrate samples for the determination of PHPA in drilling fluids. McCulley et al. propose a method based on a sulphuric acid digestion of the whole mud sample, which results in the total oxidation of organic material and a complete conversion of organic nitrogen to ammonium ions which are subsequently detected using an ammonium ion-selective electrode. These chemical methods may be used to detect the total amount of PHPA in the drilling fluid; however, in order to optimise the system, the effective concentration of PHPA (i.e. the concentration of PHPA which is free to associate with reactive shale formations and thus aid in the stabilisation of the wellbore and drilled cuttings) must be determined, not just the total concentration of PHPA. During drilling, the effective concentration of PHPA may be depleted by at least two mechanisms: (i) by adsorption on the wellbore wall and on newly drilled solids; and (ii) by polymer degradation—e.g. due to shearing through bit nozzles. Traditionally, the industry has used indirect qualitative field methods involving a subjective examination of the 'quality' of cuttings passing over the shaker screens to assess the inhibition level of a drilling fluid. If the effective PHPA concentration in the drilling fluid is too low, cuttings will become highly dispersed resulting in an accumulation of drilled solids within the circulating fluid; if the effective PHPA concentration is too high, the polymer can 'agglomerate' and 'blind' the solids control equipment screens. Williamson, L. D., Javanmardi, K. and Flodberg, K., "Method aids calculation of PHPA depletion rates", *Oil & Gas Journal,* July 1992 describes a hot rolling dispersion test at the rig site as a method for analysing the effective concentration of PHPA. The analysis depends on the ability of the drilling fluid to inhibit dispersion relative to a standard PHPA salt solution. This article emphasises that the PHPA inhibitor level should be adjusted to correspond with formation reactivity; the field data clearly indicate that the inhibitive performance index of a PHPA drilling fluid decreases as a result of interactions with formations rich in montmorillonite.

Thus, the previously proposed methods for monitoring PHPA in drilling fluids have focused on two general approaches: (i) the development of rather involved chemical techniques to determine the total PHPA concentration; and (ii) the development of indirect methods based on some diagnostic of the inhibitive performance of the fluid. The latter methods are usually based on the ability of the fluid to stabilise cuttings and not necessarily the wellbore. Similar approaches are apparent from reviewing proposed methods for determining other polymers and organics in drilling fluids. Chemical techniques for PHPA determination rely on a specific analysis of amide groups in the analyte polymer; therefore, they rely on a previous evaluation of the degree of hydrolysis of the particular PHPA used to formulate the drilling fluid, and they do not take into account changes in the degree of hydrolysis which may occur as PHPA responds to high temperature alkaline conditions. Many of the range of polymers used to provide the required rheological and fluid loss properties of drilling fluids have very similar functional groups, and, as a result, it is often difficult to develop chemical techniques which are sufficiently specific for the determination of each polymer in complex mixtures.

Previous Patents and other Publications have described methods based on Fourier Transform Infrared (FTIR) spectroscopy for determining the total concentration of both solid and organic/polymer components in water-based drilling fluids (European Pat. Appl. EP 426,232, U.S. Pat. No. 5,161,409, and European Pat. Appl. 507,405) and in oil-based drilling fluids (European Pat. Appl. EP 507,405).

It is widely recognised that the static filtration of drilling fluids containing polymers often results in an enrichment of the polymer in the filter cake and a corresponding depletion in the filtrate. McCulley et al. emphasise that the filtrate obtained from the standard API filtration apparatus is considered to be unsuitable for any truly quantitative procedure for determination of the PHPA concentration in drilling fluids. Hughes, T. L., Jones, T. G. J. and Houwen, O. H., "The chemical composition of CMC and its relationship to the rheology and fluid loss of drilling fluids", SPE 20000, presented at the IADC/SPE Drilling Conference, Houston, March 1990 concludes that the recovery of carboxymethyl cellulose (CMC) in API filtrates obtained from some simple CMC-bentonite fluids is dependent on both the polymer/bentonite ratio of the fluid and on the molecular weight distribution of the polymer.

SUMMARY OF THE INVENTION

It is an object of this invention to provide methods, based on infrared spectroscopy, for the simultaneous determination of a wide variety of organic and polymer additives (which may have very similar functionalities) in representative samples of the liquid phase of a range of water-based drilling fluids. The methods can also be used for rapid quality control testing of organic and polymer additives used in water-based drilling fluids.

The present invention provides a method of quantitative analysis of free organic components in a drilling fluid, the method comprising the steps of: separating solid and liquid components of the drilling fluid using a non-filtering technique; taking a sample of the liquid components, and mixing this sample with a solution of an inorganic carrier; analysing the sample or the mixture using infrared spectroscopy so as to determine the amount of organic components in the mixture; and deriving the amount of free organic components in the drilling fluid from this analysis.

The mixture of the liquid components sample and an inorganic carrier is dried to leave a solid mixture of the organic components and the carrier. In this case, the mixture is preferably analysed using a reflectance technique such as diffuse reflectance infrared spectroscopy. In another embodiment, the liquid component is analysed directly, preferably using a direct transmission technique. In both the liquid and solid cases, Fourier transform infrared spectroscopy is preferred.

A convenient non-filtering separation technique is centrifugation, which can be performed until the amount of solids in the supernatant or "centrate" is sufficiently low that their interference with the analysis can be ignored.

The present invention has certain advantages over the Prior Art methods. The use of a non-filtering separation technique means that there is no depletion of the organic component by absorption in the filter cake, and so the measurement is representative of the free concentration of the component in the drilling fluid. The organic components can be quantified simultaneously, and if required certain inorganic components can be quantified as well. The method uses liquid samples and carrier solutions which can be measured volumetrically rather than by weight. This is an advantage when operating on floating rigs such as semisubmersible drilling rigs or drill ships where the vertical motion of the rig due to wave action interferes with the operation of weighing devices and so prevents accurate quantitative analyses.

BRIEF DESCRIPTION OF THE DRAWINGS

The invention will now be described both by way of the following illustrative Examples and with reference to the accompanying Drawings, in which.

DESCRIPTION OF THE EMBODIMENTS OF THE INVENTION

Example 1

The method according to the invention obtains a representative sample of the liquid phase of water-based drilling fluids for analysis. The validity of the method can be demonstrated by comparing the composition of representative samples of the liquid phase of simple water-based drilling fluids with the composition of filtrates obtained using the standard API filtration apparatus.

In this Example, a representative sample of the liquid phase of a water-based drilling fluid is obtained by centrifuging the fluid using a microcentrifuge. In general, the application of a 20,000 g force for 10 minutes is sufficient to reduce the residual solids in the 'centrate' to a level which will not interfere with the infrared analysis of polymer and organic components.

Figure 1:
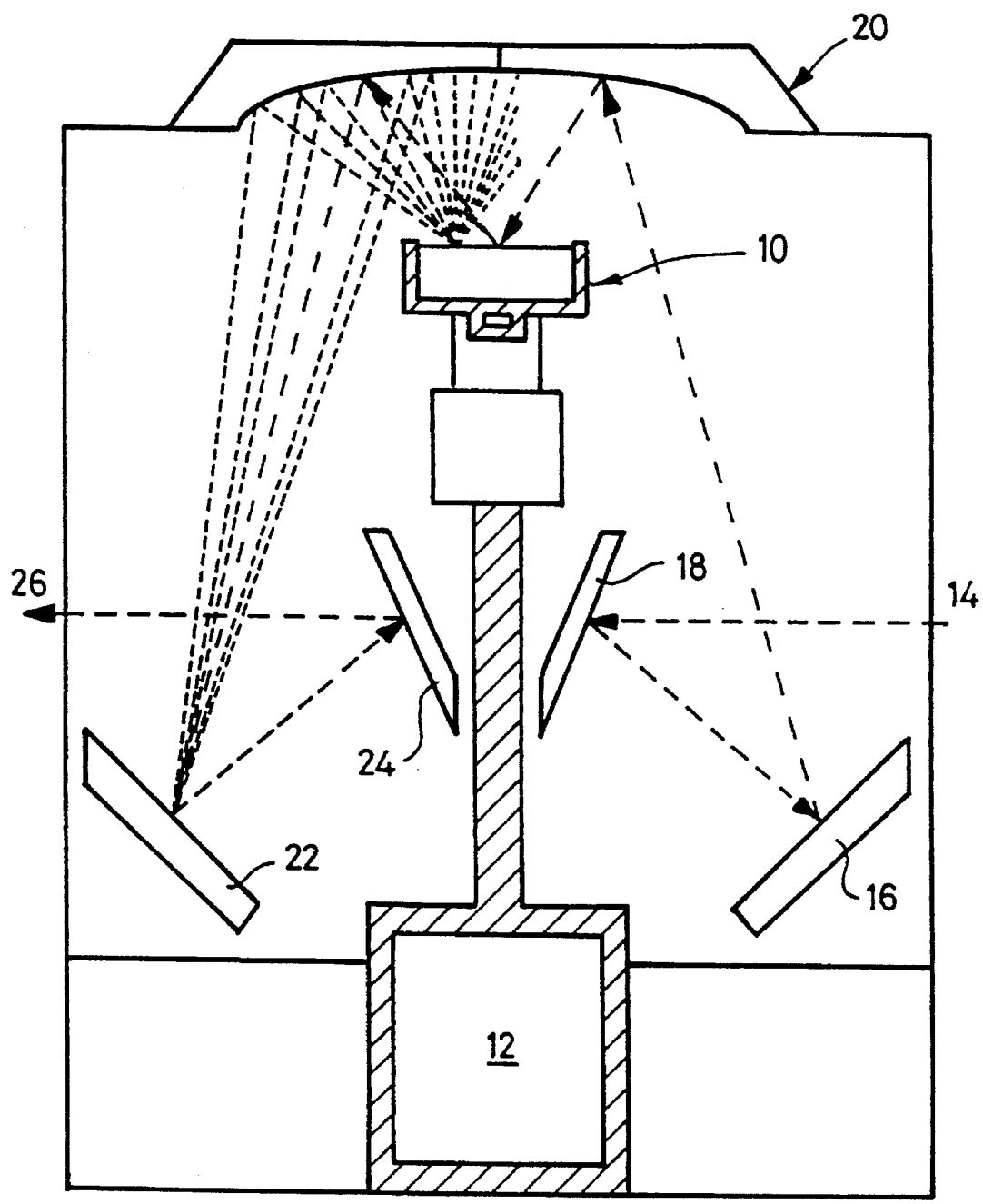
FIG. 1 shows a DRIFTS cell used for Example 1.

The analysis technique used here comprises a diffuse-reflectance infra-red Fourier transform spectrometry (DRIFTS) technique such as is described in Griffiths, P. R. and Fuller, M. P., "Mid infrared spectrometry of powdered samples", in "Advances in Infrared and Raman Spectroscopy: Volume 9", R. J. H. Clark and R. E. Hester (Eds.), Heydon & Son Ltd. (1982) for measuring the FTIR spectrum of an analyte aqueous solution containing organic and polymer additives and dissolved salts. The DRIFTS cell used for spectral measurements is shown schematically in FIG. 1, and comprises a cup 10 for holding the sample to be analysed, mounted on a motor 12 to allow rotation during scanning. The sample is irradiated from an IR source 14 via plane mirrors 16, 18 and an ellipsoid mirror 20 mounted above the sample cup 10. The ellipsoid mirror 20 also reflects the specular and diffuse reflectance from the sample, via further mirrors 22, 24, to a detector 26.

The analysis involves the following sample preparation and measurement steps:

a) add 1 ml of the analyte solution (centrate) to 1 ml of a 2 molar potassium bromide (KBr) solution, and mix;

b) transfer the mixture onto a drying pan, and remove its water fraction by heating to 160° C.;

c) transfer the dried solid to a pestle and mortar, and crush lightly to produce a fine powder;

d) transfer the fine powder to a DRIFTS sample cup using a small compaction cell device; apply 20 kg load to the powder in the cup for one minute prior to levelling the surface of the sample;

e) measure the DRIFTS spectrum of the sample by ratioing against a 'background' prepared using a mixture of 1 ml deionised water and 1 ml of the 2 molar KBr solution.

For the application of this procedure to an analyte solution containing 1 g/l polymer, the dried solid sample/KBr mixture contains (calculated) 0.001 g polymer (0.42 wt. % of the mixture) and 0.238 g potassium bromide (99.58 wt. % of the mixture). Thus, the dried mixture is dominated by the potassium bromide matrix, and, as a result, has very similar properties to the background preparation when lightly crushed to a fine powder and compacted/levelled prior to the collection of its spectrum. Since the analyte sample is mixed with potassium bromide in solution, the analyte polymer is extremely well mixed, at the molecular level, within the resultant dried mixture. This high degree of homogeneity results in highly reproducible spectral measurements for replicate applications of the procedure.

Figure 2:
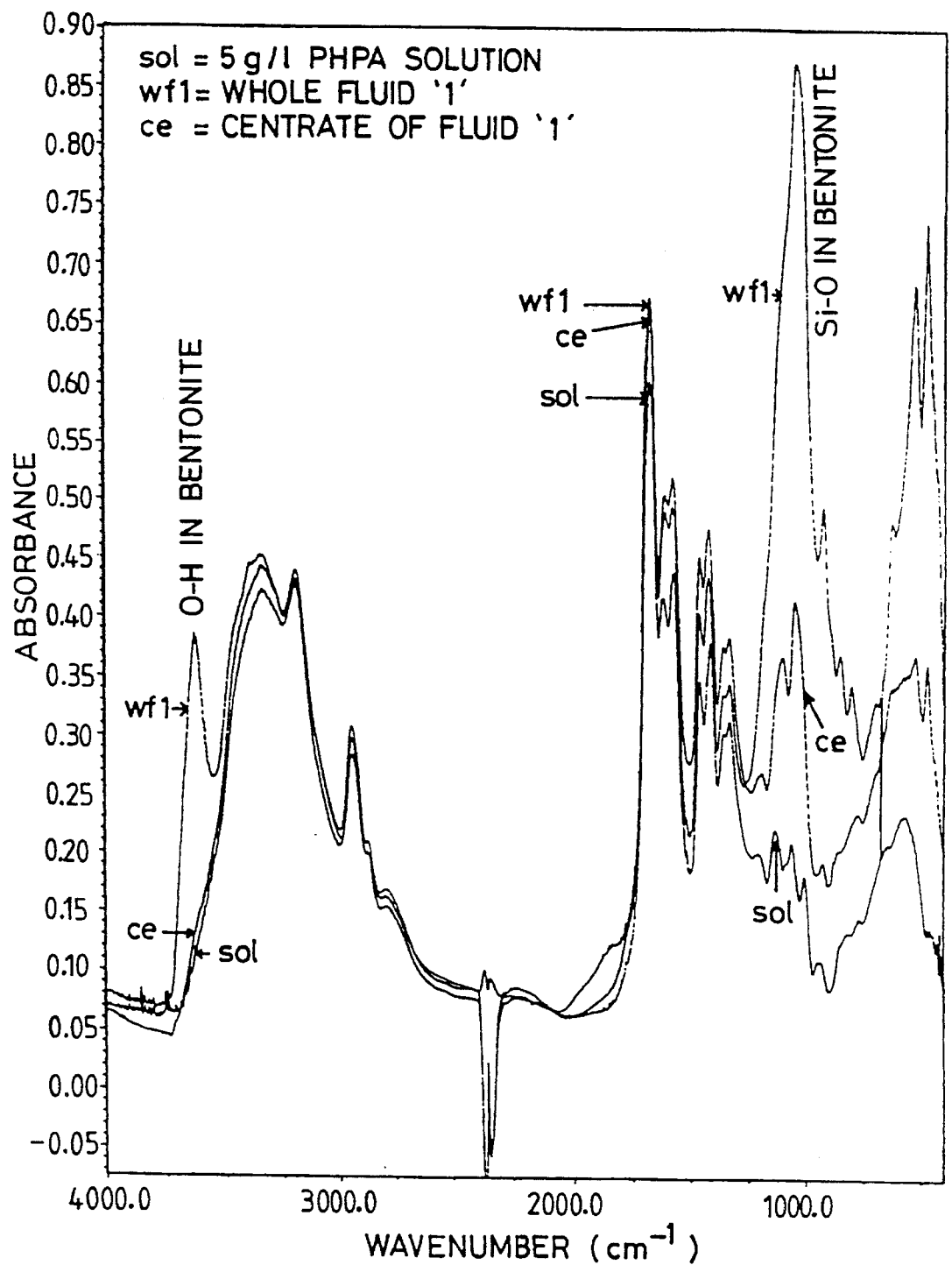
FIG. 2 shows spectra of (i) a solution containing 5 g/l PHPA and 5 wt. % KCl, (ii) a whole fluid '1' containing 15 g/l bentonite, 5 g/l PHPA and 5 wt. % KCl, and (iii) the centrate (20000 g force, 10 minutes) of fluid '1' for Example 1.
Figure 3:
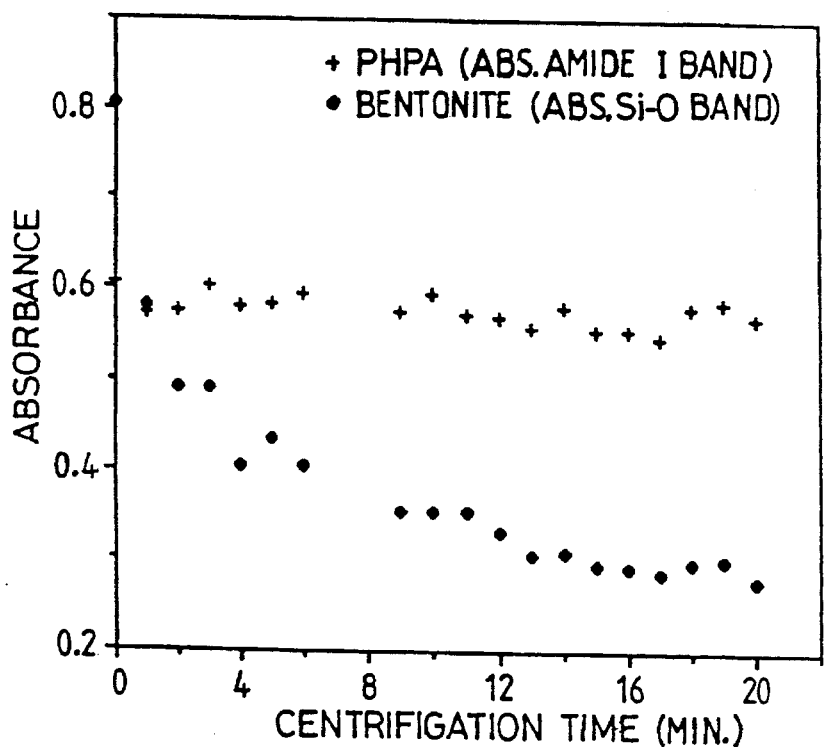
FIG. 3 shows effect of centrifugation time (20000 g force) on absorbances due to residual bentonite and PHPA in the centrate in Example 1.

FIG. 2 demonstrates the effect of centrifugation by comparing the spectra of: (i) a solution containing 5 g/l PHPA and 5 wt. % KCl; (ii) a whole fluid '1' containing 15 g/l bentonite, 5 g/l PHPA and 5 wt. % KCl; and (iii) the centrate (20,000 g force, 10 minutes) of fluid '1'. The absorbance peak at 3620 cm$^{-1}$ is due to stretching vibrations of O—H bonds in the bentonite component; the peaks at 1030, 521 and 464 cm$^{-1}$, due to fundamental Si—O vibrations, are also characteristic of bentonite. The absorbance peaks due to bentonite are suppressed but not completely absent in the centrate spectrum. FIG. 3 shows the effect of centrifugation time (at constant 20,000 g force) on the absorbance of (i) the main bentonite Si—O band (1030 cm$^{-1}$) and (ii) the main PHPA Amide I band (1668 cm$^{-1}$) in the centrate spectra. The trends indicate that most of the bentonite is removed from the centrate after around 5 minutes centrifugation. By comparison, the effect of centrifugation time on absorbance due to PHPA in the centrate is small. However, the absorbance of the main PHPA Amide I band shows a gradual decrease with time which is attributed to a decreasing contribution by residual fines. The data serve to demonstrate that most of the larger and more dense solid particles in a drilling fluid will be rapidly transported to the base of the centrifuge tube during the first few minutes of centrifugation. In contrast to the filtration process, centrifugation does not involve movement of the liquid phase through a low permeability filter cake, and, as a result, the concentration of polymer in the final 'centrate' is representative of that in the liquid phase of the original fluid.

Figure 4:
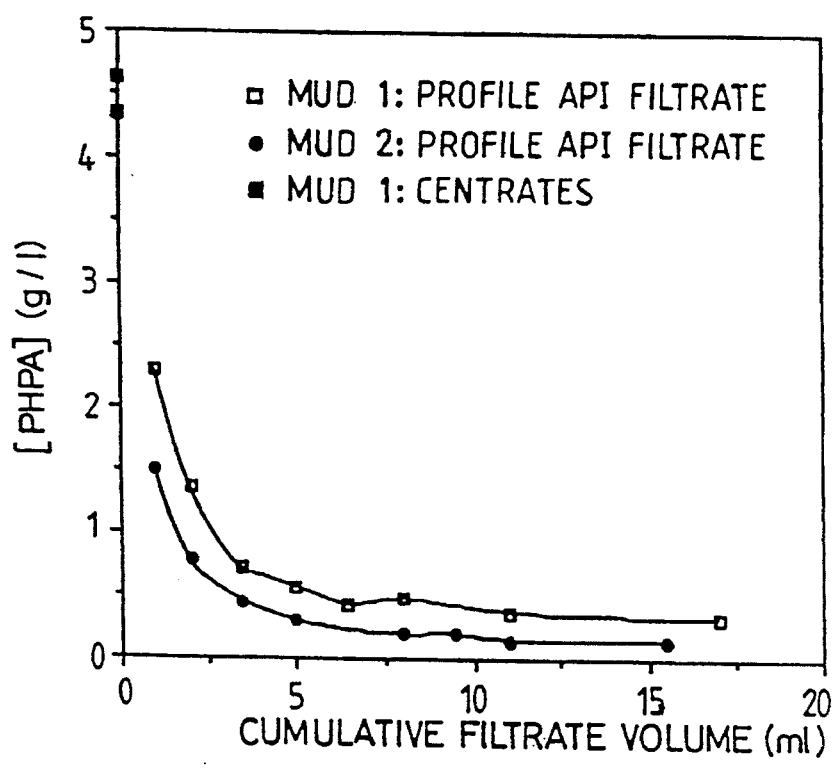
FIG. 4 shows comparison of [PHPA] (g/l) in the centrate and successive aliquots of API static filtrate.

FIG. 4 compares the concentrations of PHPA in centrates and API static filtrate samples prepared from duplicate muds containing 15 g/l bentonite, 5 g/l PHPA and 5 wt. % KCl. The centrates contain around 4.5 g/l PHPA; this indicates that around 30 mg PHPA is adsorbed on each gram of bentonite in the original muds. In contrast, the API static filtrate samples contain considerably lower concentrations of PHPA. As the static filtration process proceeds, PHPA is increasingly excluded from the filtrate; a near constant PHPA concentration (around 0.3–0.5 g/l) is recovered in the filtrate after the static filter cake has reached a steady state.

Figure 5:
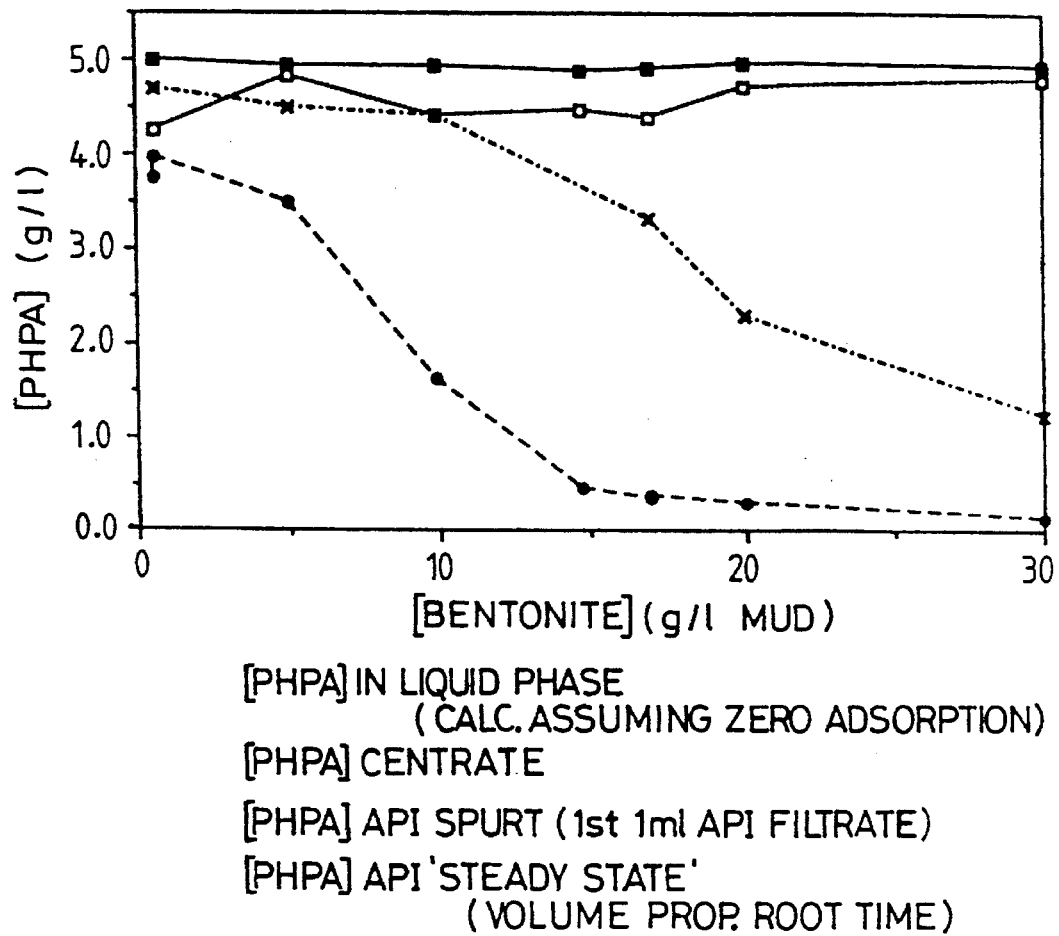
FIG. 5 shows analyses of PHPA in the centrate, API 'spurt' and API 'steady state' filtrates in Example 1. It shows the effect of the bentonite content in the original fluid.

FIG. 5 compares the concentrations of PHPA in centrates, API 'spurt' filtrate samples and API 'steady state' filtrate samples as a function of the bentonite content (0.5–30 g/l) of a series of muds containing a constant 5 g/l PHPA and 5 wt. % KCl. Whilst the API 'spurt' filtrate (i.e. the first 1 ml of filtrate) may be representative of the liquid phase of the muds containing less than 10 g/l bentonite, there is an increasing degree of PHPA depletion in spurt samples as the bentonite content of the original mud increases from 10 to 30 g/l. The spectra of centrate, API spurt and API steady state filtrate samples obtained from two muds in the series are compared in FIGS. 6 (5 g/l bentonite) and 7 (20 g/l bentonite). For each mud, the spurt sample contains the highest concentration of solids.

Figure 8:
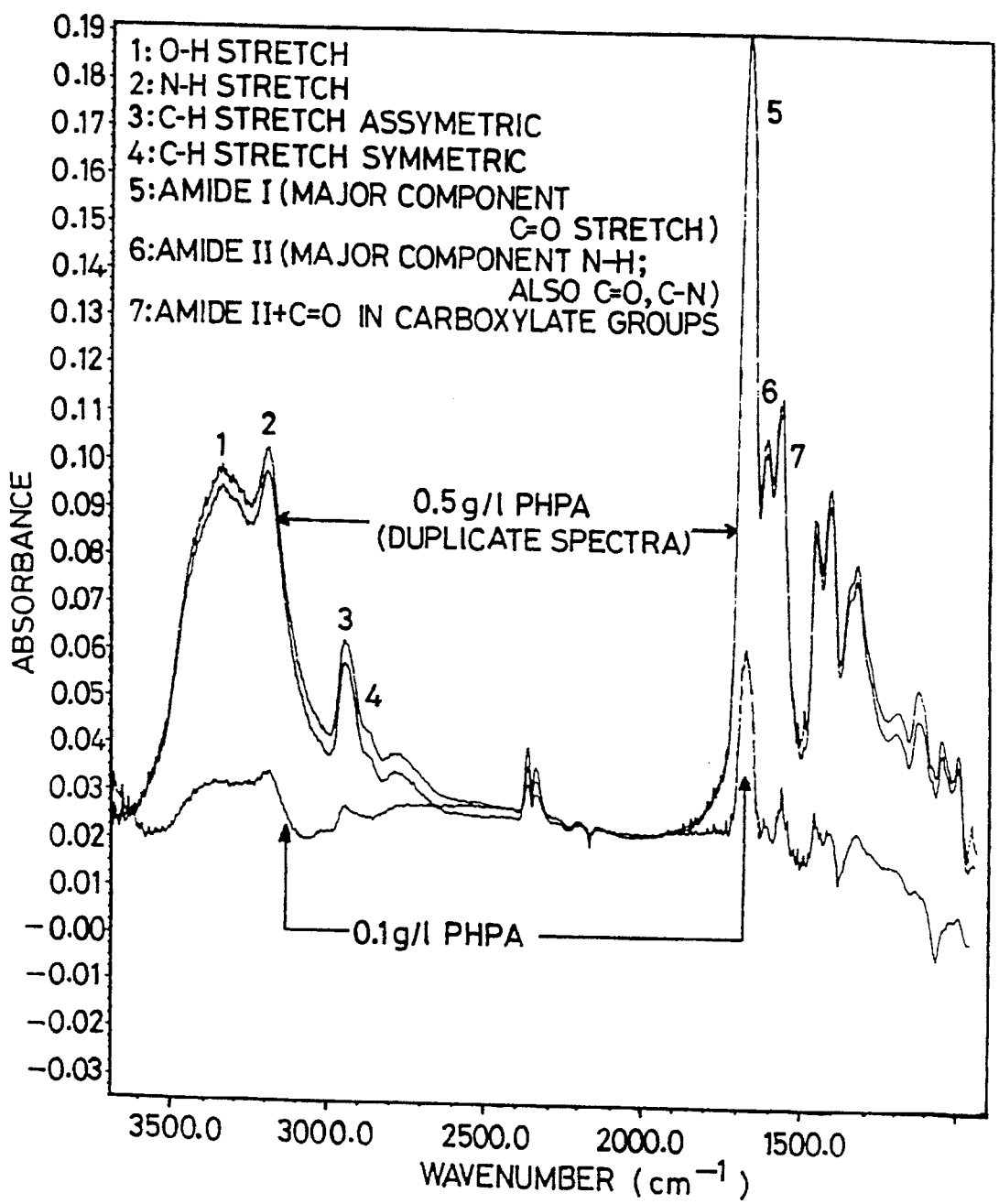
FIG. 8 shows spectra of solutions containing 0.5 g/l and 0.1 g/l PHPA from Example 1.

FIG. 8 shows duplicate spectra of a 0.5 g/l PHPA solution and a single spectrum of a 0.1 g/l PHPA solution; the major absorption bands in spectra are assigned to specific bond vibrations within the polymer. The duplicate spectra serve to demonstrate the typical reproducibility for analyses of solutions using this procedure; the main Amide I band lies in the most reproducible wavenumber region. The lower limit of detection for PHPA in solution, using this procedure, is less than 0.1 g/l.

Figure 9:
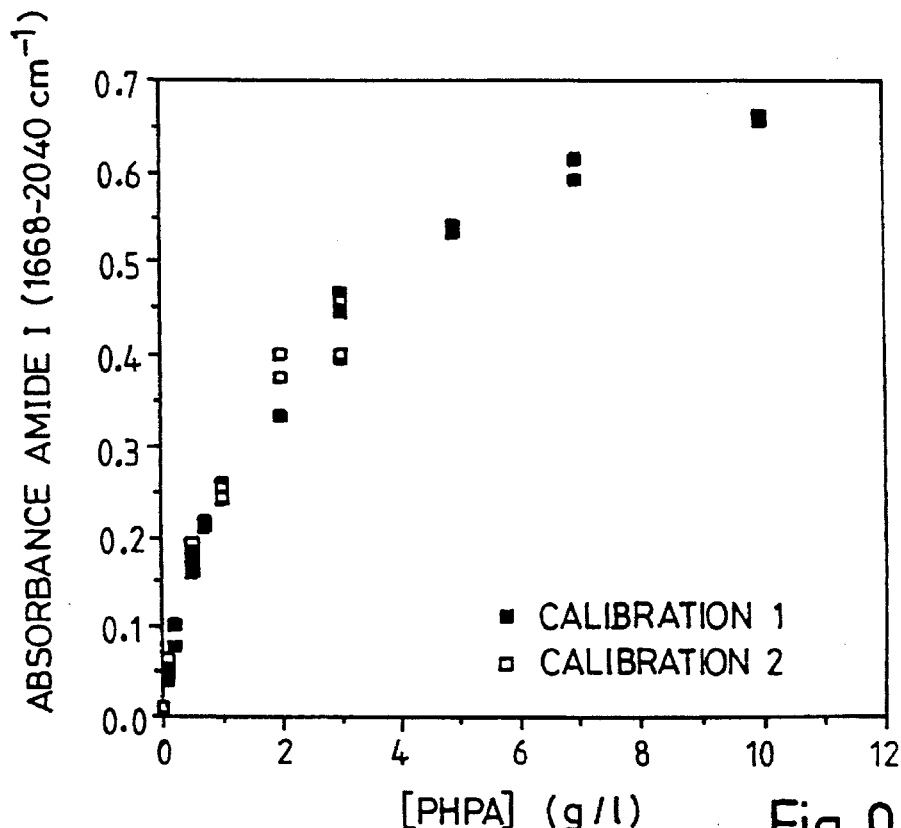
FIG. 9 shows peak height calibrations for PHPA in Example 1. It shows a plot of Absorbance Amide I band versus [PHPA ] (g/l).

FIG. 9 shows the relationship between Amide I absorbance and PHPA concentration for a series of solutions containing 5 wt. % potassium chloride; the reproducibility of the relationship is given by comparing Calibrations 1 and 2 which relate to two different sets of PHPA solutions analysed by two different operators on two different occasions. The PHPA calibration relationship shows highest sensitivity in the lower concentration range and an increasing negative deviation from the Beer-Lambert law as concentration increases.

Figure 10:
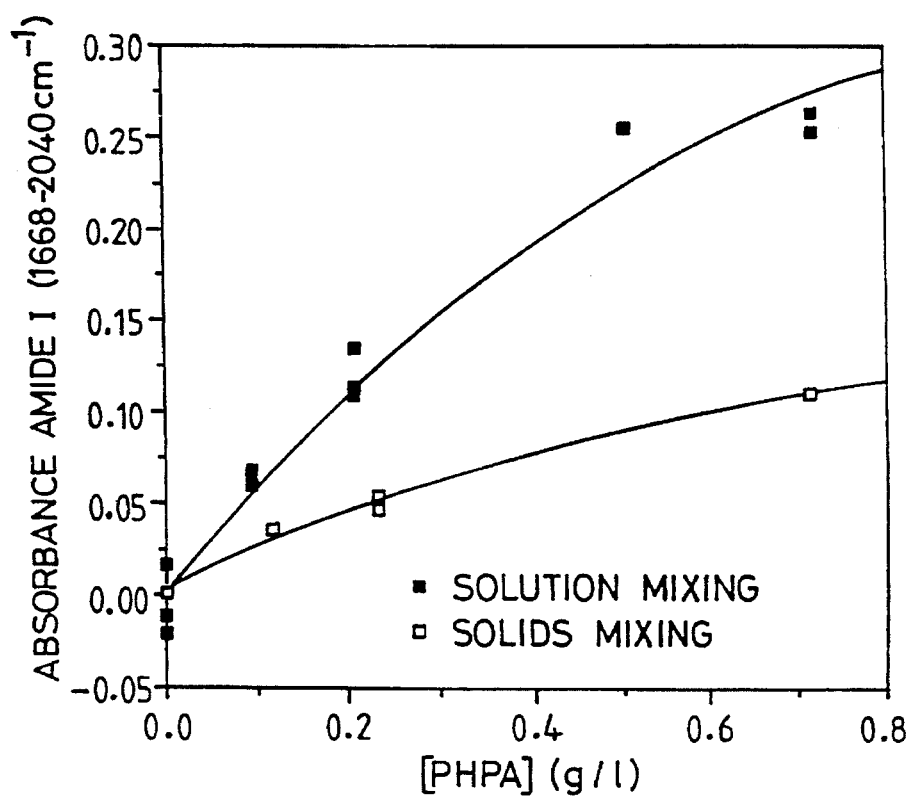
FIG. 10 shows Amide I peak height calibrations for PHPA. It provides a comparison of sensitivity for PHPA/KBr mixtures prepared by Example 1 and by Example 2.

FIG. 10 demonstrates the sensitivity enhancement obtained by mixing the analyte polymer with potassium bromide in the solution form rather than the more conventional application of DRIFTS involving the dispersion of solid analyte polymer within a matrix of solid particles of potassium bromide. As mentioned previously, an additional advantage of the use of a solution method, calibrated by volume, is that the procedure does not require the use of an analytical balance which can be problematical in certain environments such as on semisubmersible offshore drilling rigs.

A linearisation of the typical calibration relationship shown in FIG. 8 can be achieved by using the widely recognised Kubelka-Munk (K-M) transform. The K-M transform relates a function of $R_\infty$ (the ratio of diffuse reflectance from the sample to that of the non-absorbing background) to the absorptivity, a, and concentration, c, of the analyte component and to a scattering coefficient, s, by:

$$f(R_\infty) = (1-R_\infty)^2/2R_\infty = 2.303ac/s \quad (1)$$

i.e., $f(R_\infty)$ is linearly related to c if s is kept constant.

Figure 6:
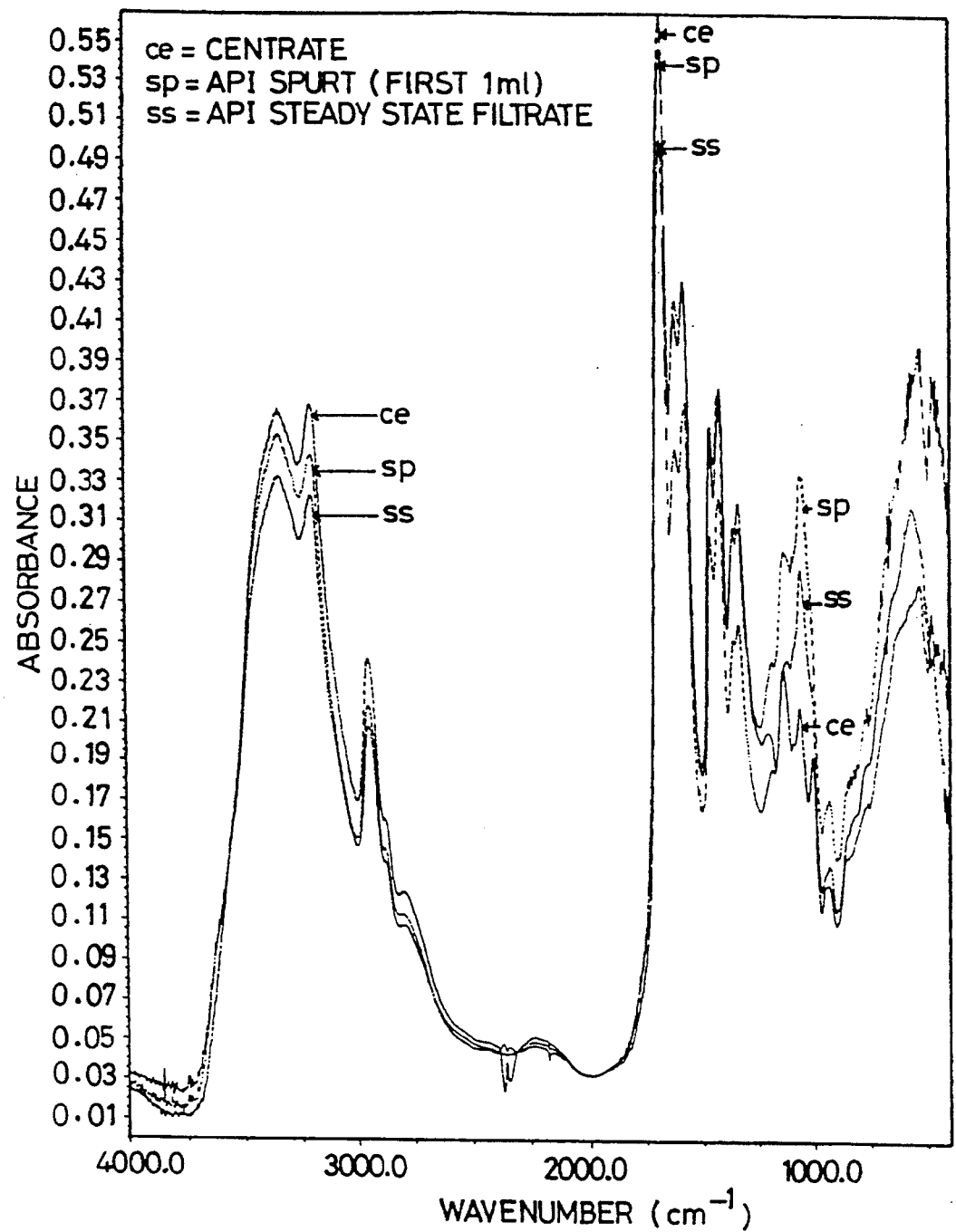
FIG. 6 shows spectra of the centrate, API 'spurt' and API 'steady state' filtrate of fluid containing 5 g/l PHPA, 5 g/l bentonite and 5 wt. % KCl for Example 1.
Figure 7:
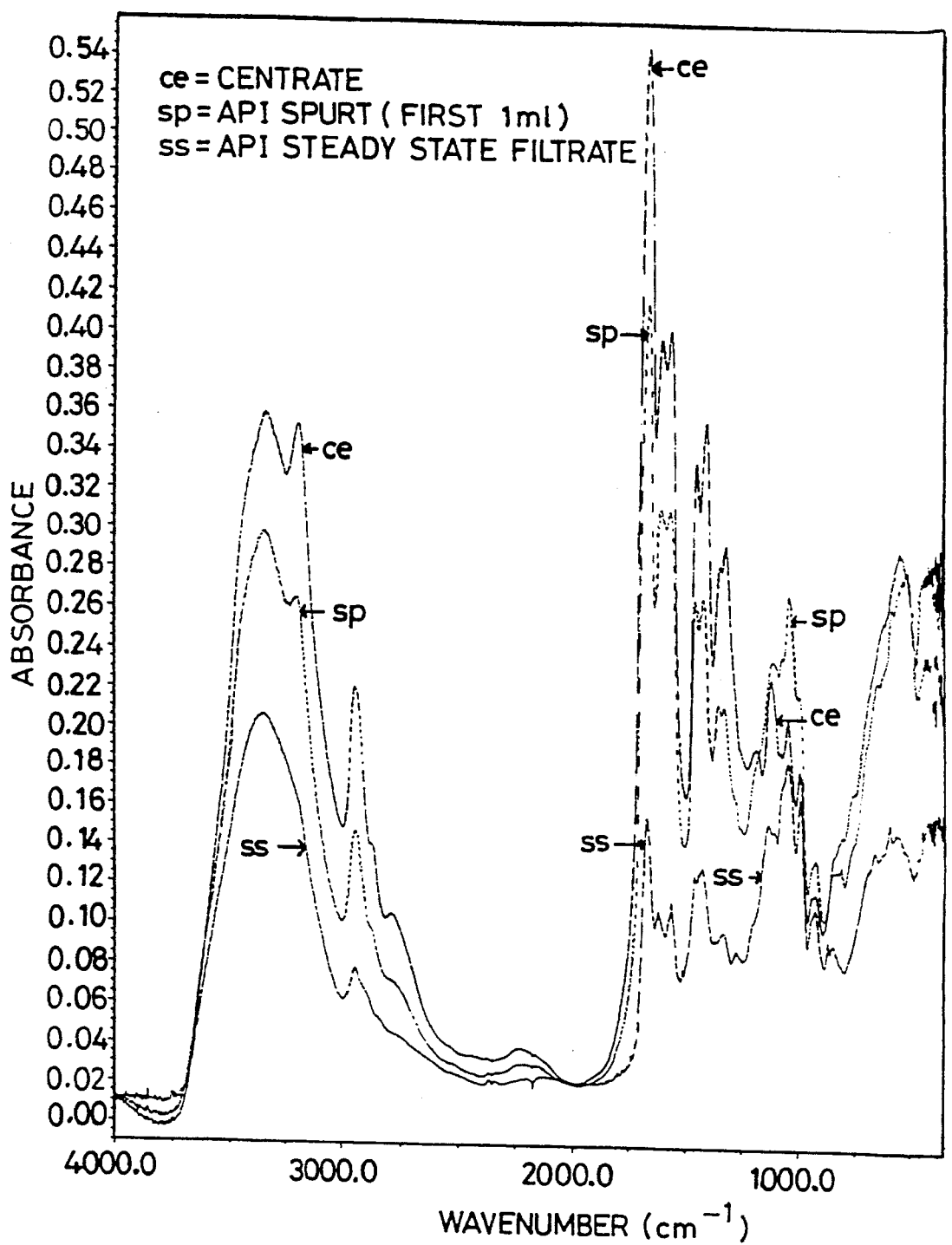
FIG. 7 shows spectra of the centrate, API 'spurt' and API 'steady state' filtrate of fluid containing 5 g/l PHPA, 20 g/l bentonite and 5 wt. % KCl for Example 1.
Figure 11:
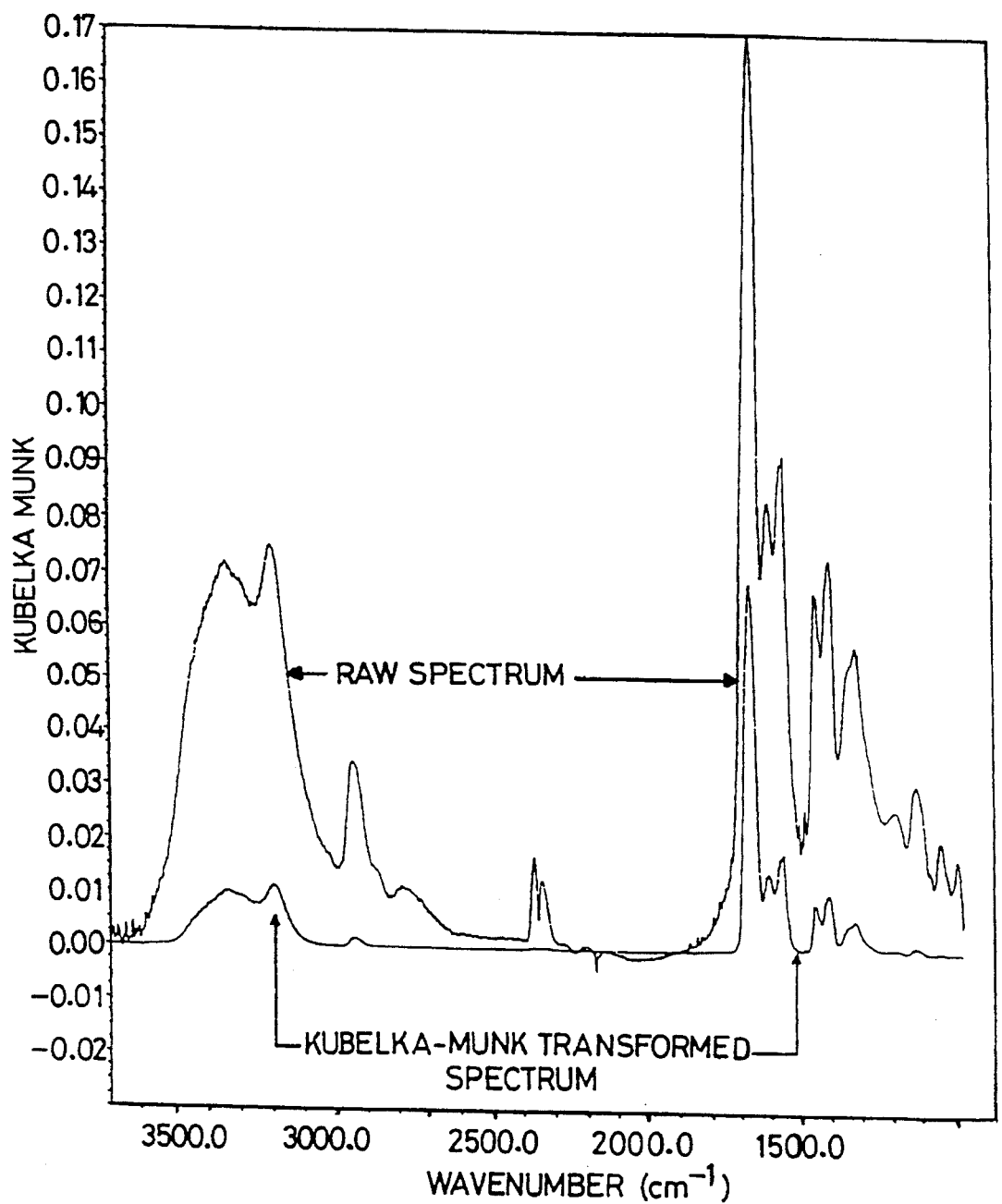
FIG. 11 shows 'Raw' and Kubelka-Munk transformed spectra of 0.5 g/l PHPA for Example 1.

FIG. 11 compares the 'raw' and K-M transformed DRIFTS spectrum of a solution of 0.5 g/l PHPA. FIG. 6 compares the linear K-M calibration relationship between $(1-R_\infty)^2/2R_\infty$ and c with the non-linear relationship between raw absorbance, $A=\log_{10}(1/R_\infty)$ and c for the Amide I band.

Figure 12:
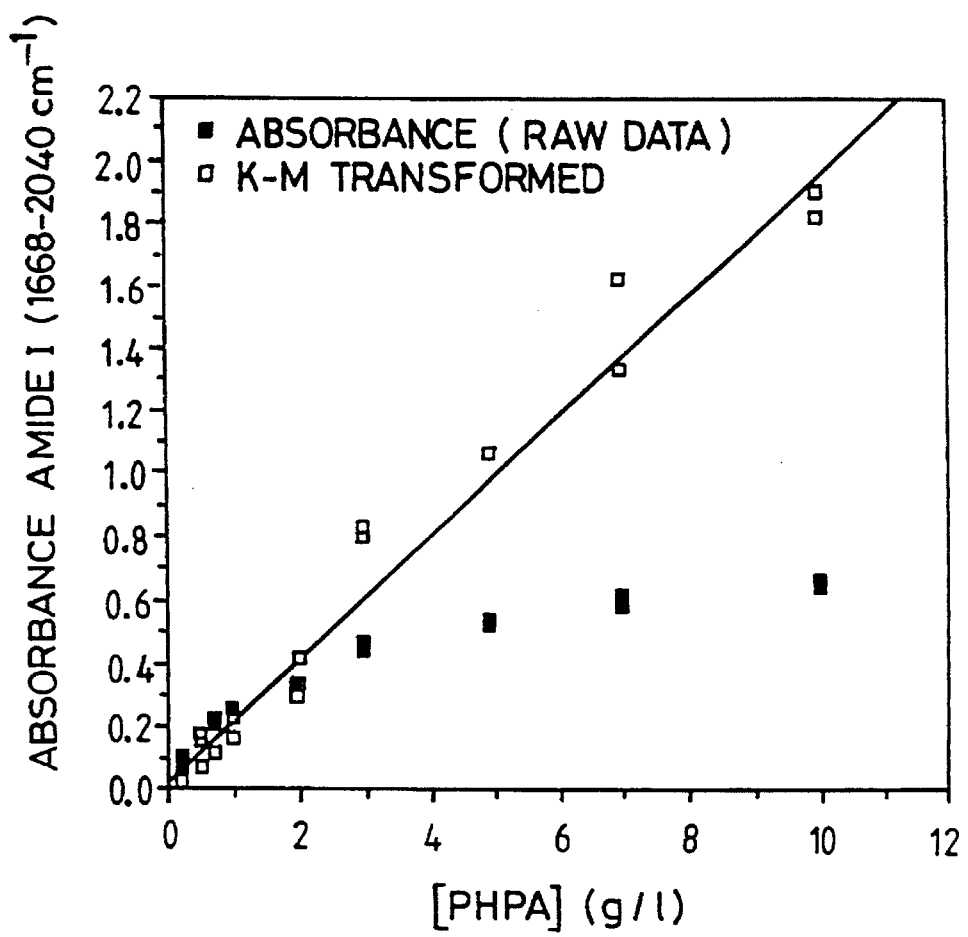
FIG. 12 shows peak height calibrations for PHPA In Example 1. It provides a comparison of raw absorbance with K-M transformed data.
Figure 13:
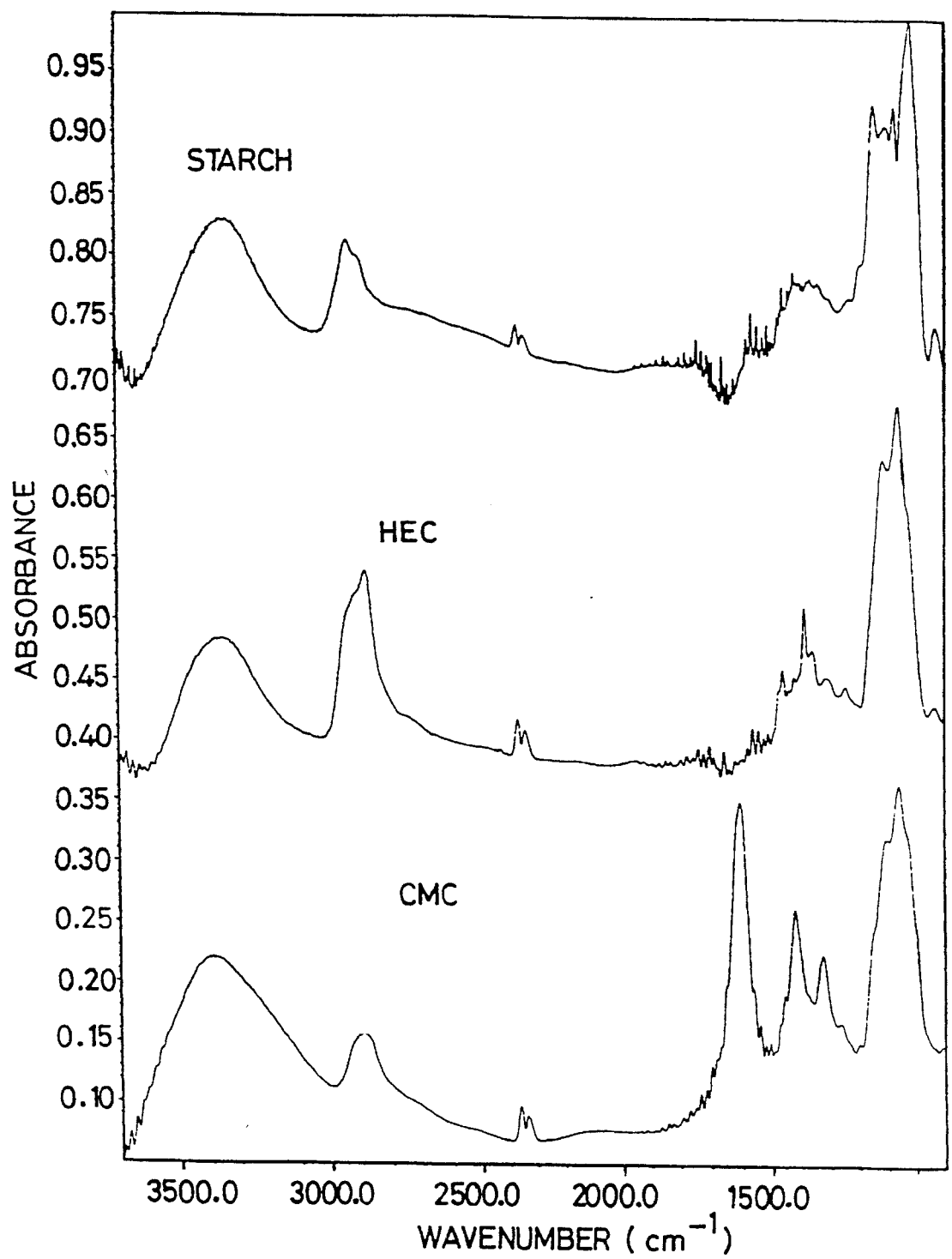
FIG. 13 shows spectra of 1 g/l solutions of starch, hydroxyethyl cellulose (HEC) and carboxymethyl cellulose (CMC) from Example 1.
Figure 14:
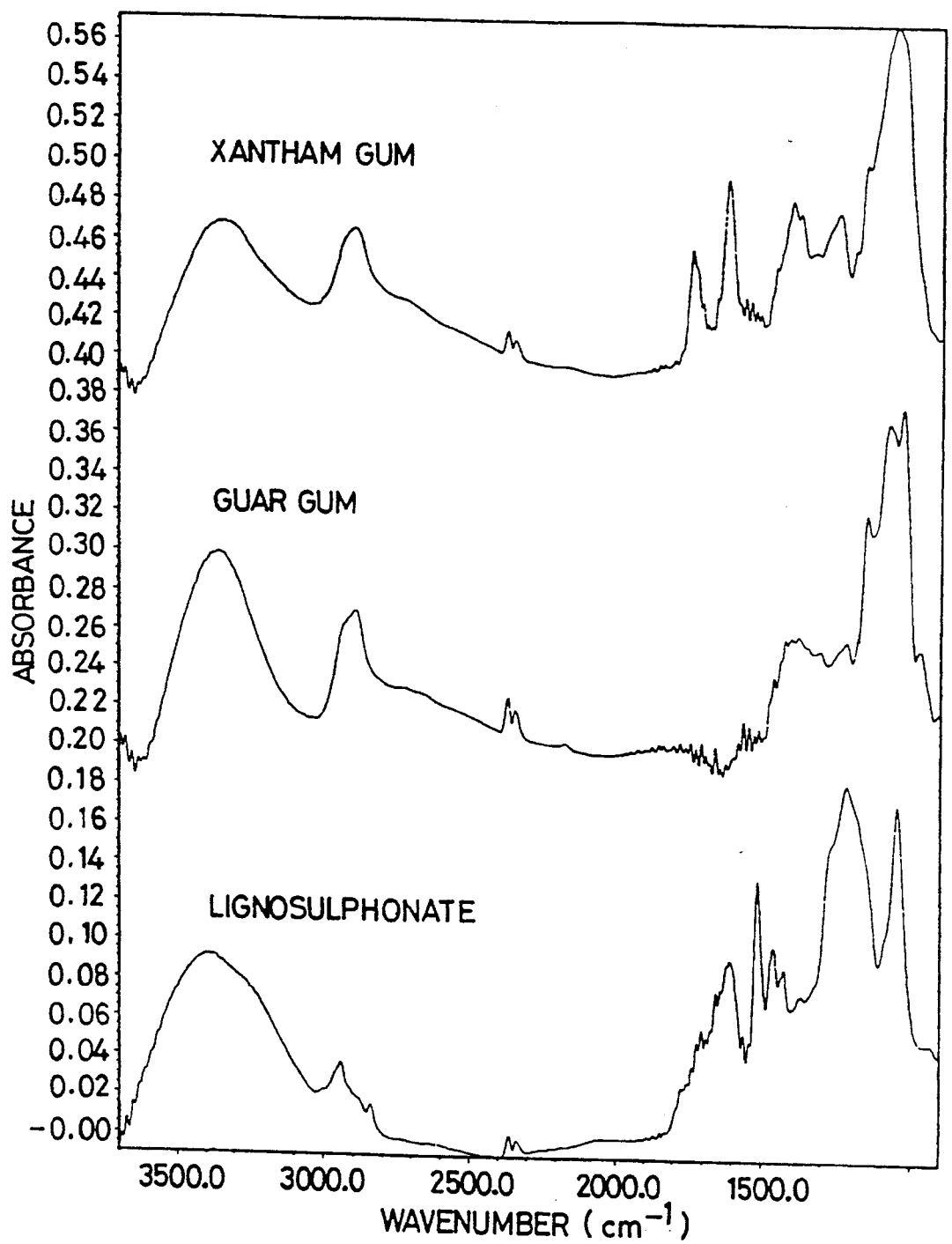
FIG. 14 shows spectra of 1 g/l solutions of xanthan gum, guar gum and lignosulphonate from Example 1.

FIGS. 12 and 13 show DRIFTS spectra for 1 g/l solutions of a broad range of polymers used in water-based drilling fluids. The data demonstrate the specificity of the technique in discriminating polymers which have similar functionalities. For example, the DRIFTS spectra of starch and guar gum are sufficiently different to enable their discrimination and quantification using multivariate deconvolution techniques.

Figure 15:
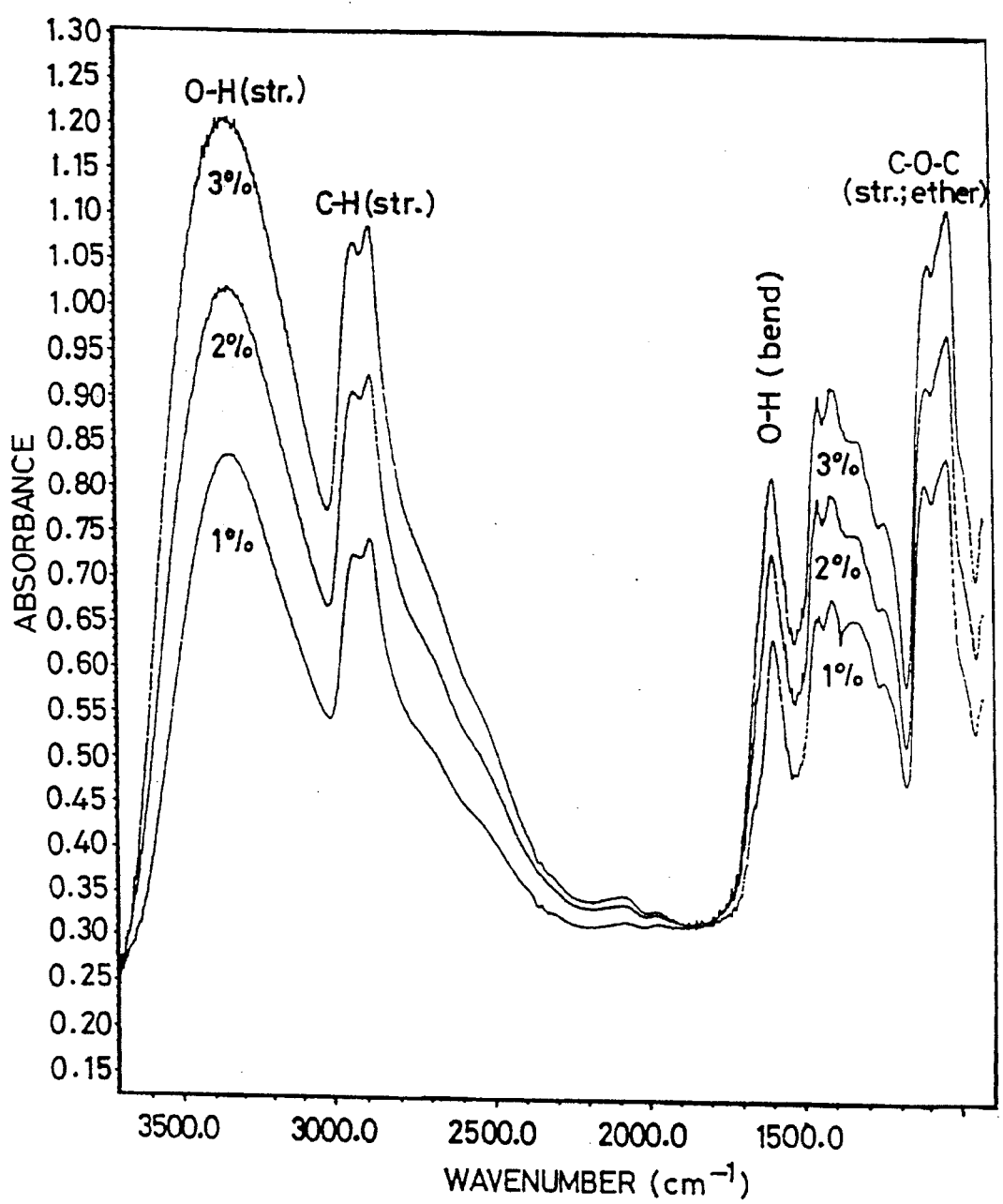
FIG. 15 shows spectra of solutions containing 1–3% (v/v) polyglycerol from Example 1.
Figure 16:
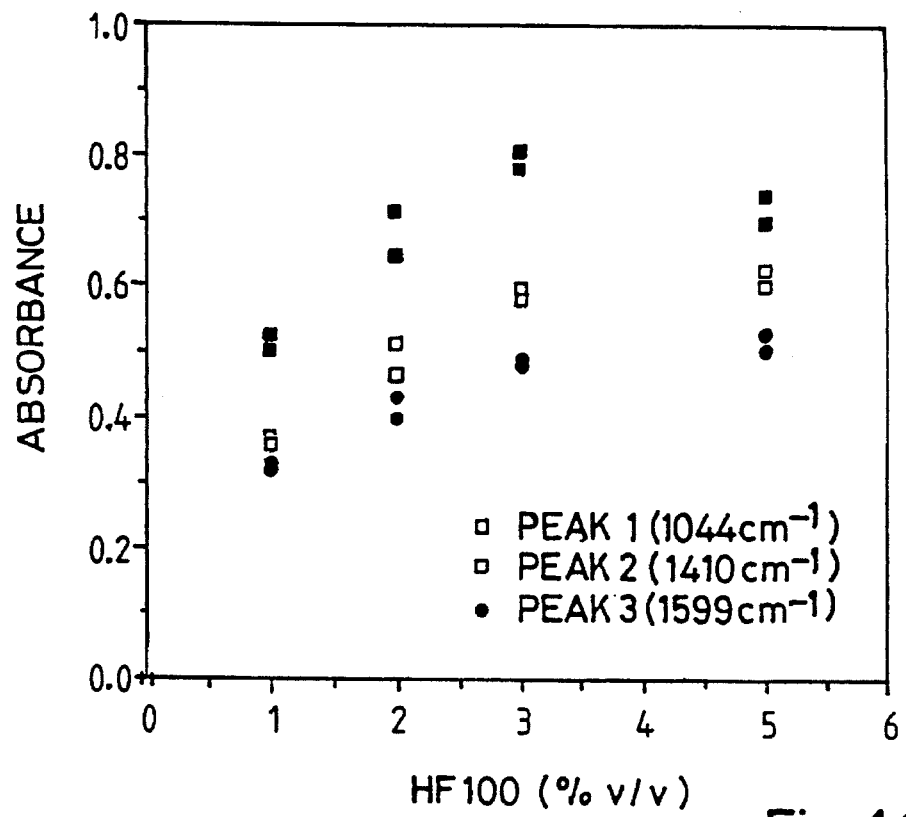
FIG. 16 shows peak height calibrations for polyglycerol product. It shows a 'saturation' of Example 1 as product concentration increases >3% (v/v).

The useful concentration range of certain organic additives in water-based drilling fluids is considerably higher than that of the more traditional polymers used for rheology, fluid loss and shale stabilisation. Notably, the 'polyols' (polyglycols and polyglycerols) may be used in concentrations up to 15% by volume, although the more usual range is around 3–8% by volume. FIG. 15 shows DRIFTS spectra for a series of solutions containing a polyglycerol additive in the concentration range 1–3% by volume. The spectra indicate that systematic increases in the height of the main absorbance bands can be used to quantify the product when it is present in concentrations up to 3% by volume. However, as shown in FIG. 16 for absorbance bands 1, 2 and 3, systematic relationships between absorbance and concentration break down when the concentration of the product is above 3% by volume. Thus, prior to an application of this procedure to the analysis of higher concentrations ($\geq 3\%$ by volume) of organic additives such as the 'polyols', it is necessary to introduce an extra sample preparation step involving either (i) a dilution of the analyte sample solution (e.g. by a factor of 5 using deionised water) or (ii) a decrease in the volume of analyte solution (e.g. by a factor of 5) added to 1 ml of the 2 molar potassium bromide solution.

Example 2

Figure 17:
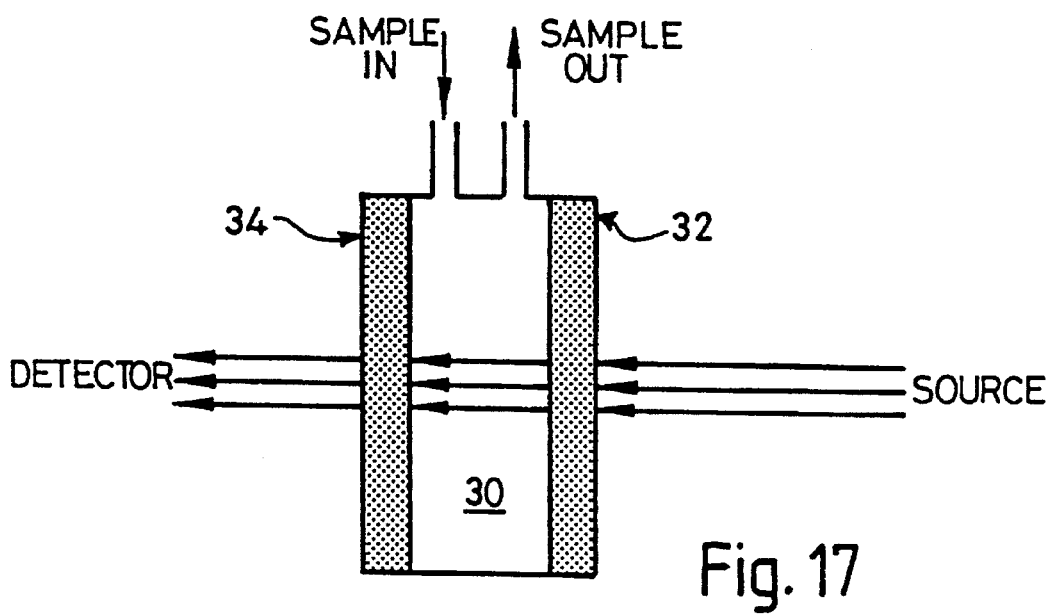
FIG. 17 shows a variable pathlength transmission cell used for Example 2.

This example uses the transmission FTIR spectrum of an analyte solution containing organic and polymer additives and dissolved salts. The arrangement used for the measurements is shown in FIG. 17, and comprises a variable pathlength transmission cell 30, fitted with inert barium fluoride windows, 37, 34. The pathlength of the cell 30 can be varied, the optimum length being 40 microns. The procedure involves the following simple measurement steps:

a) measure the transmission background spectrum of deionised water using a pathlength for which the signal/noise ratio is optimum.

b) increase the distance between the barium fluoride windows prior to displacing the water with the analyte sample solution. Readjust the cell to the optimum pathlength and measure the transmission spectrum of the analyte solution with respect to the water background spectrum.

c) in order to prevent 'memory' effects, the cell should be dismantled and cleaned thoroughly with deionised water between successive measurements of analyte sample solutions.

Figure 18:
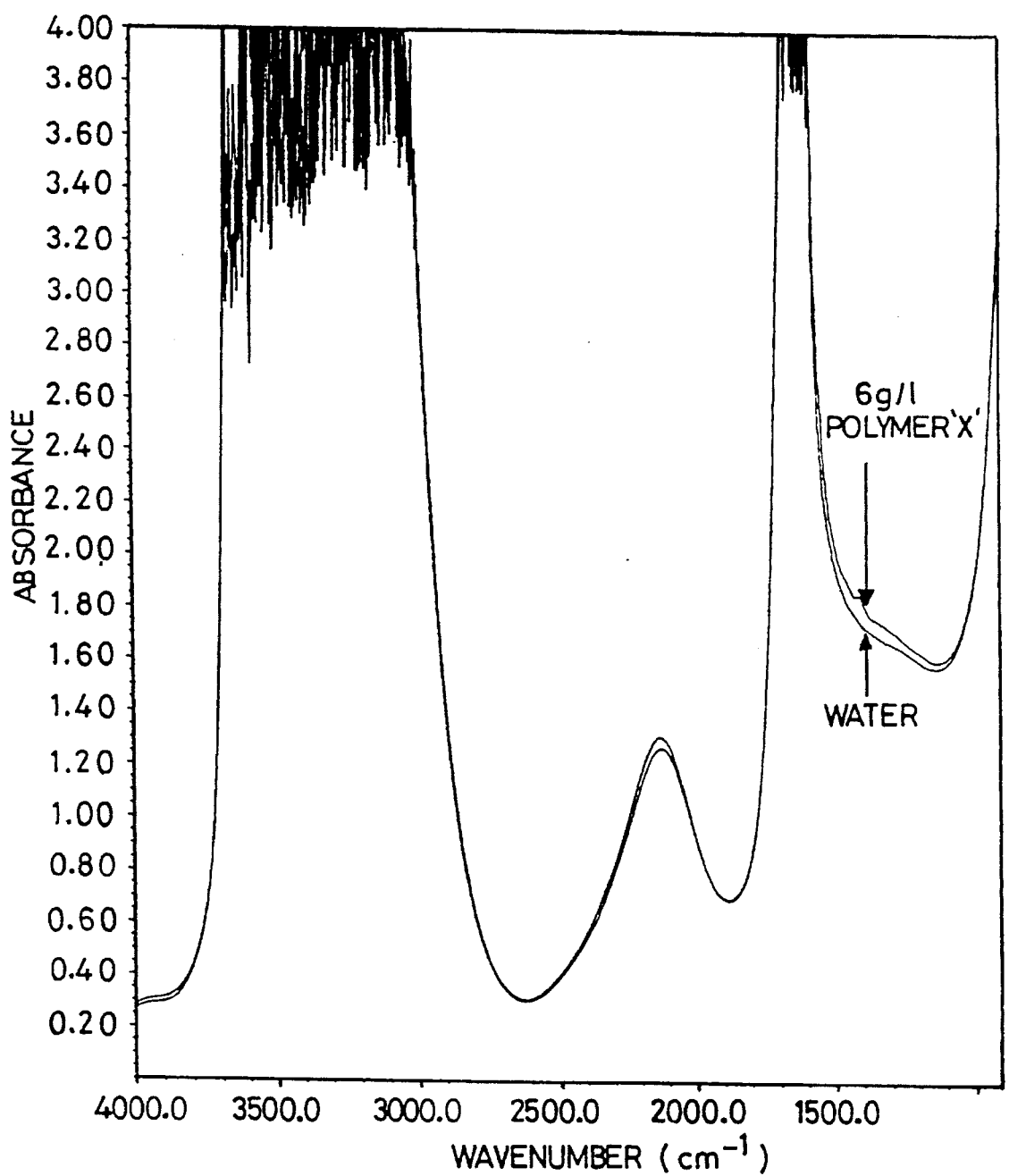
FIG. 18 shows spectra of pure water and a 6 g/l solution of polymer 'X' for Example 2.
Figure 19:
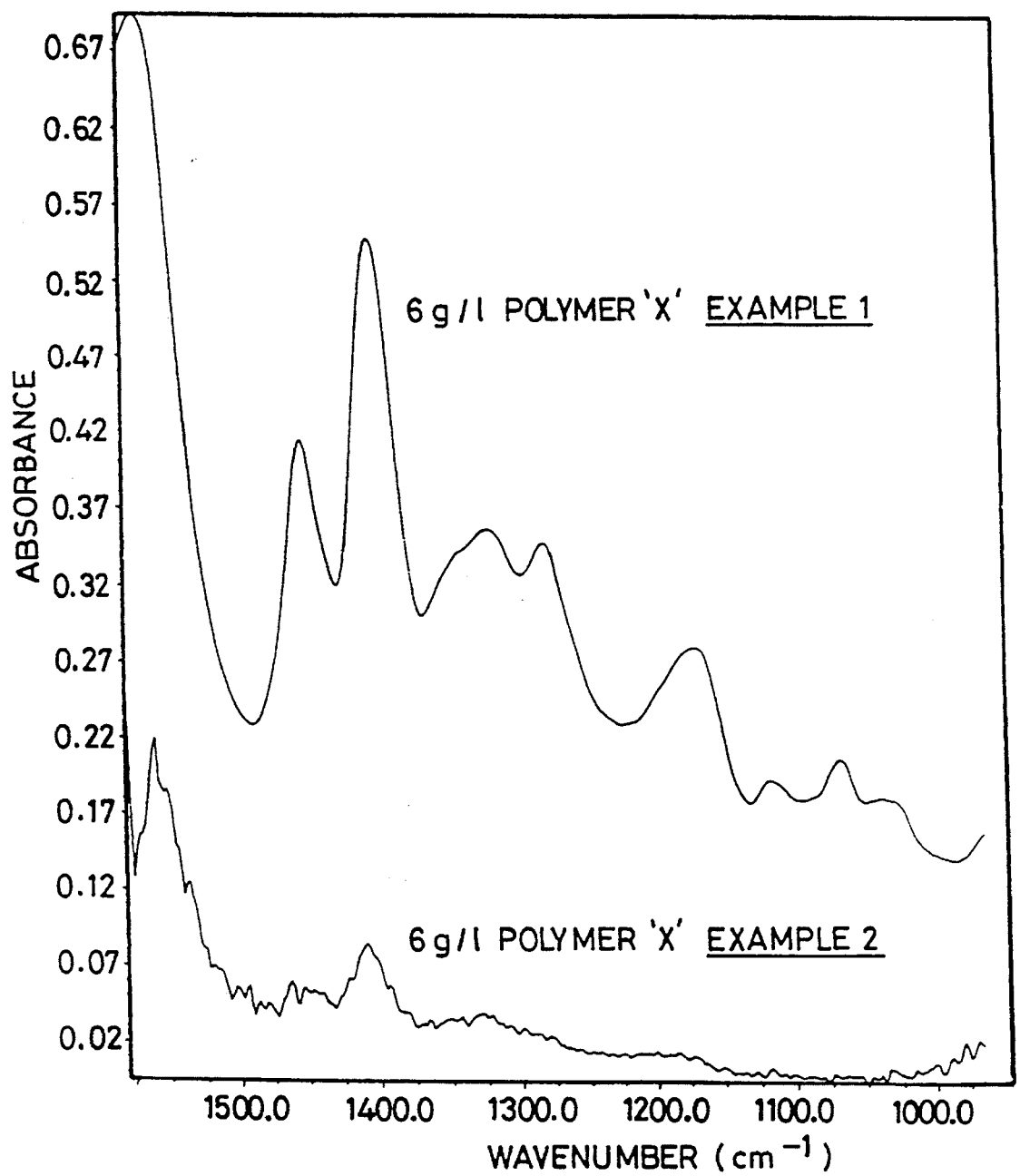
FIG. 19 shows spectra of 6 g/l solution of polymer 'X' for both Examples 1 and 2.

FIG. 18 compares the transmission FTIR spectra of pure water (with respect to an air background) and that of a solution containing 6 g/l of inhibitive polymer X (with respect to the same background). Both spectra are dominated by absorbance due to water with O—H stretching (3700–3000 cm$^{-1}$) and bending (1700–1580 cm$^{-1}$) modes of vibration producing highly intense and noisy data. Absorbance due to the analyte polymer is confined to the wavenumber region 1580–1000 cm$^{-1}$, with a specific absorbance peak due to carboxylate groups in the analyte occurring at 1408 cm$^{-1}$. FIG. 19 compares, on an equivalent absorbance scale, the transmission spectrum of the solution containing 6 g/l inhibitive polymer X (with respect to a water background) with the DRIFTS (Example 1) spectrum of the same solution. The main absorbance bands in the transmission spectrum are due to carboxylate (1556 and 1408 cm$^{-1}$), and are well correlated with equivalent bands in the DRIFTS spectrum; however, as expected, interactions of carboxylate groups with solvent molecules cause significant shifts in transmission band frequencies with respect to equivalent bands in the DRIFTS spectrum.

Figure 20:
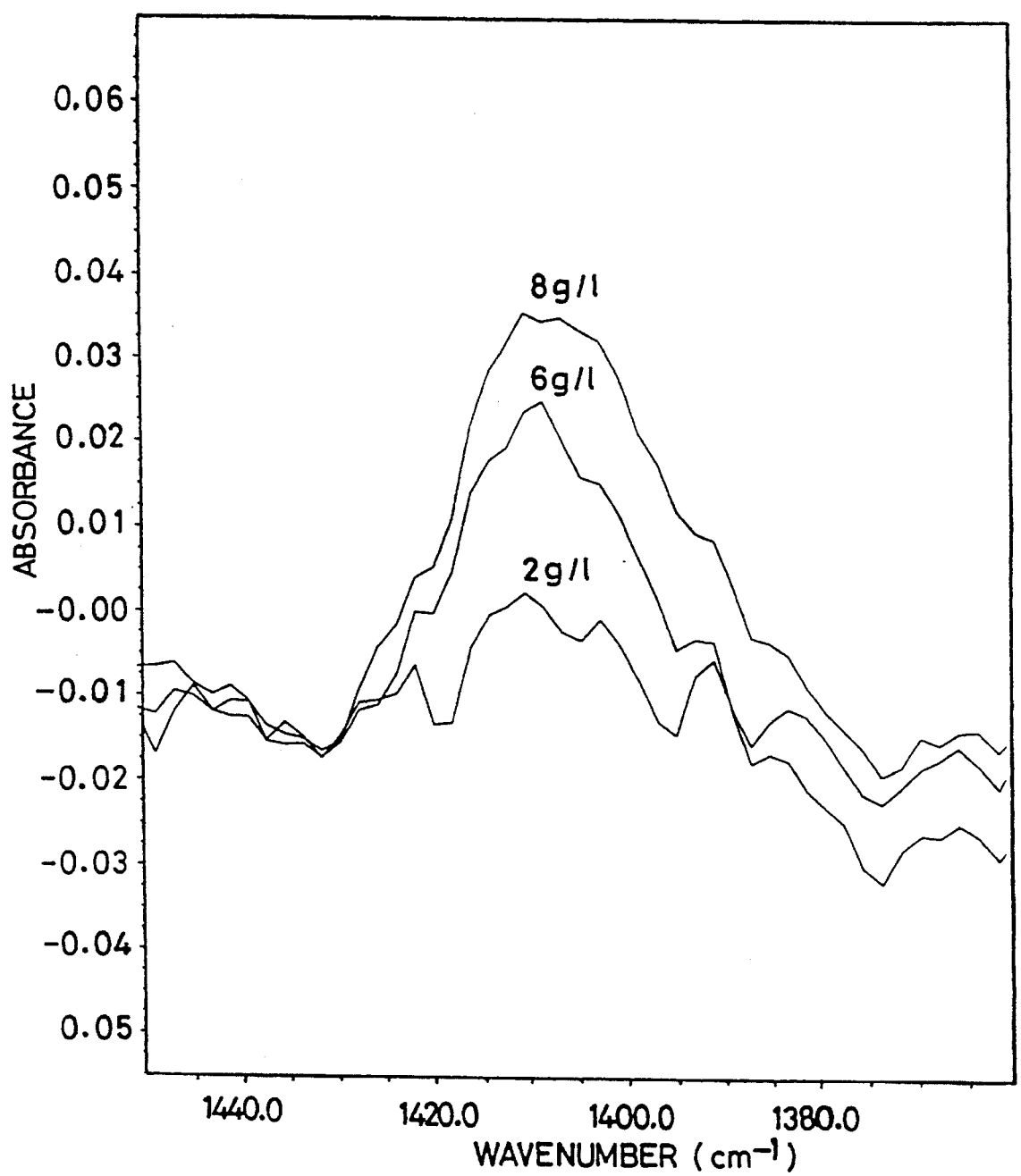
FIG. 20 shows spectra (1408 cm$^{-1}$ band) as a function of [polymer 'X'] for Example 2.
Figure 21:
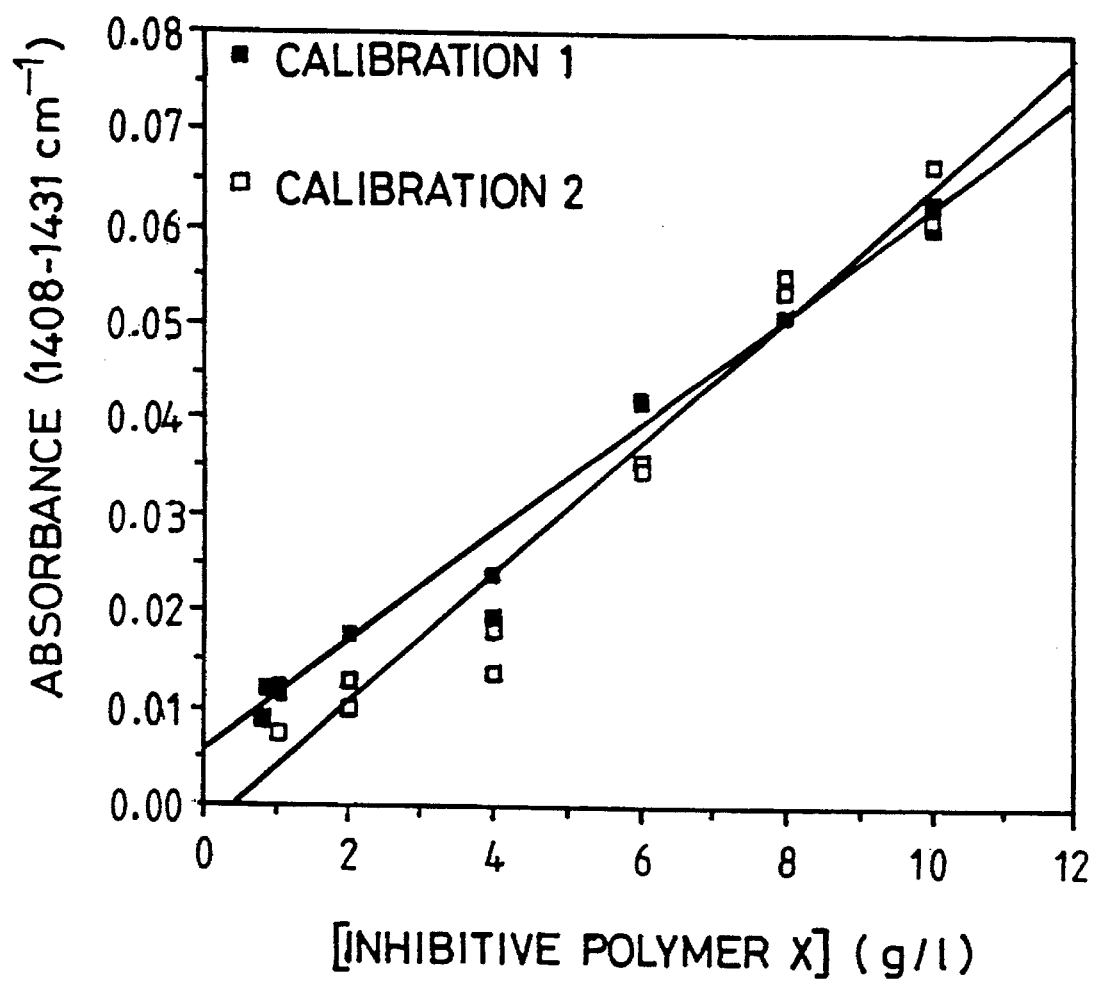
FIG. 21 shows peak height calibration for inhibitive polymer 'X' for Example 2. It plots Absorbance (1408 cm$^{-1}$) versus [polymer 'X'] (g/l).

FIG. 20 shows a systematic increase in the absorbance of the 1408 cm$^{-1}$ band as the concentration of the analyte polymer increases. FIG. 21 shows linear calibration relationships between peak height (1408 cm$^{-1}$ band) and polymer concentration up to 10 g/l; calibrations 1 and 2 were collected using two different pairs of transmission cell windows and by two different operators on two different occasions. The data indicate that the lower limit of detection of inhibitive polymer X in solution using the transmission procedure is around 1 g/l.

Figure 22:
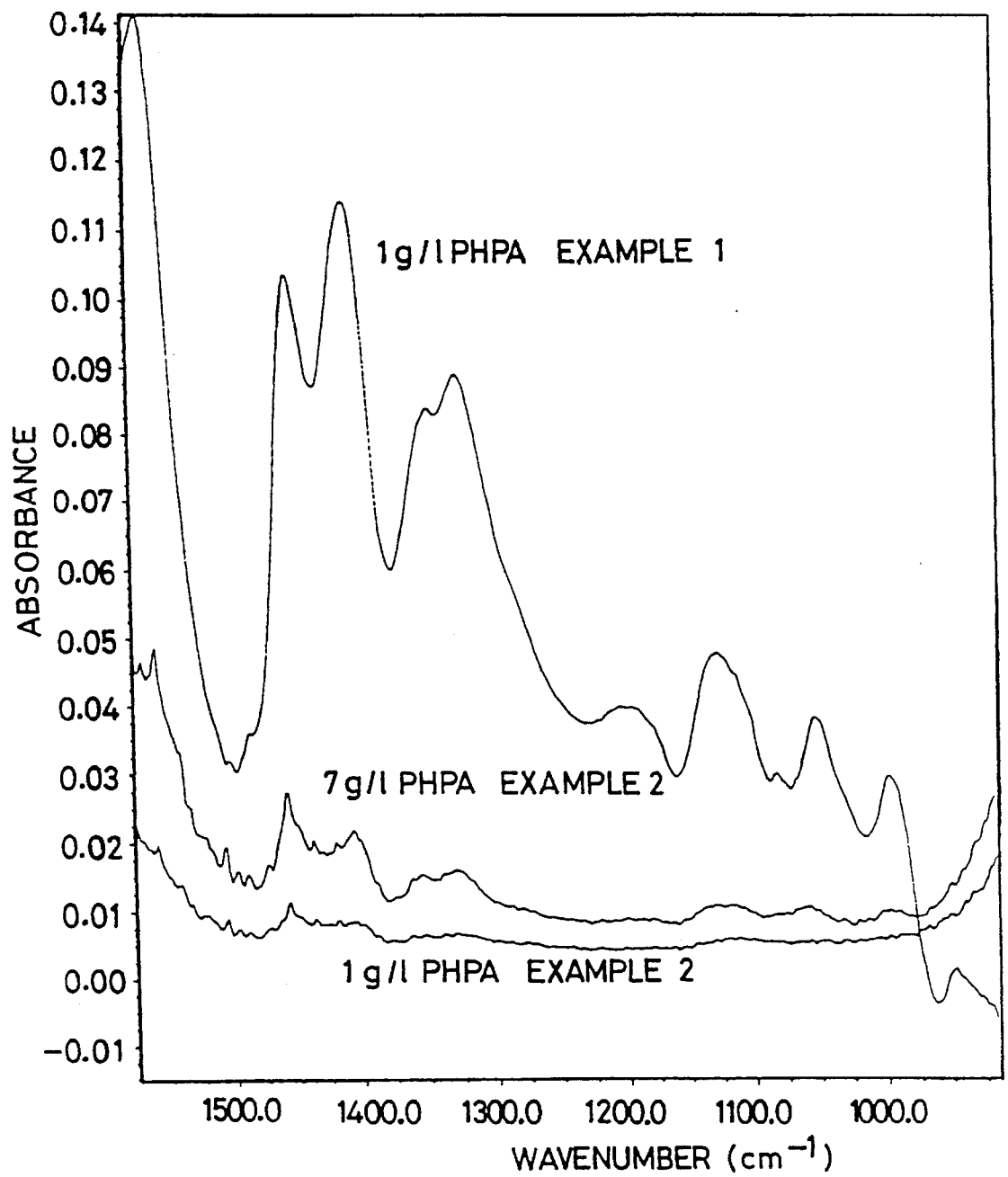
FIG. 22 shows spectra of 1 g/l and 7 g/l PHPA solutions for Example 2 and spectrum of 1 g/l PHPA solution for Example 1.
Figure 23:
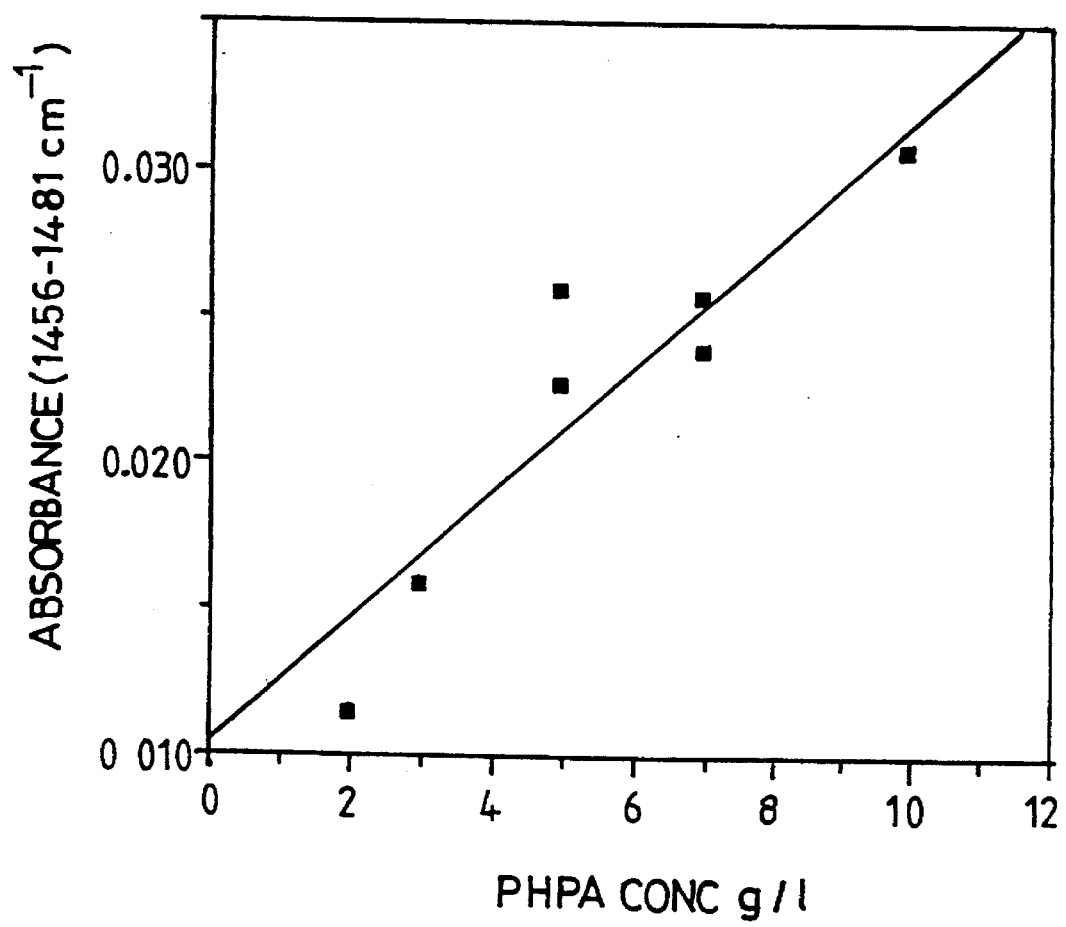
FIG. 23 shows peak height calibration for PHPA for Example 2. It plots absorbance (1456 cm$^{-1}$ band) versus [PHPA] (g/l).

FIG. 22 compares, on an equivalent absorbance scale, the transmission spectra of solutions containing 1 and 7 g/l PHPA with the DRIFTS spectrum of the solution containing 1 g/l PHPA. Again, the main absorbance bands in the transmission and DRIFTS spectra are well correlated with significant frequency shifts due to polymer-solvent interactions in the solution sample. FIG. 23 shows the linear relationship between peak height (1456 cm$^{-1}$ band) and PHPA concentration up to 10 g/l. The data in FIGS. 22 and 23 indicate that the lower limit of determination of PHPA in solution, using transmission, is around 1 g/l.

Figure 24:
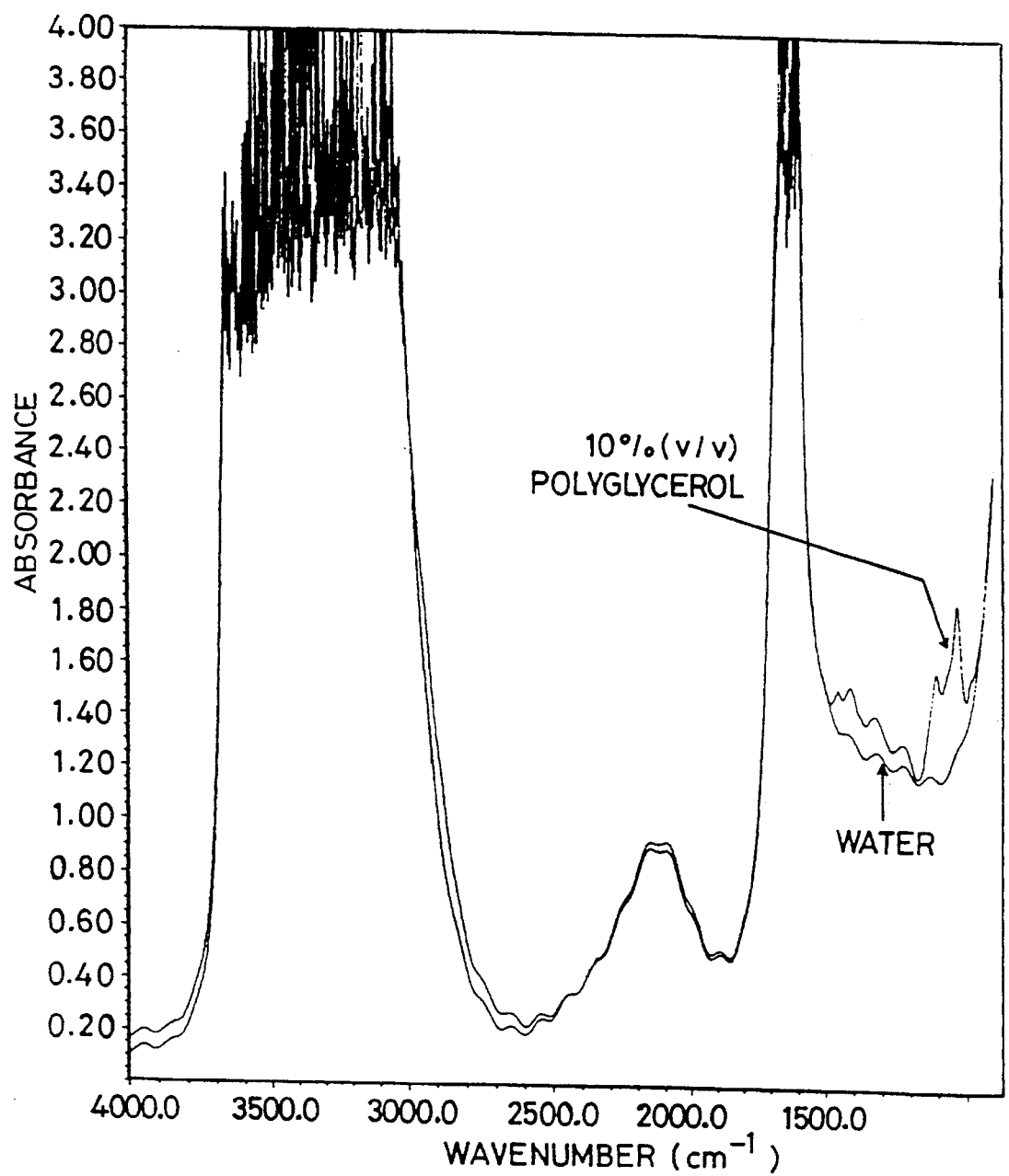
FIG. 24 shows spectra of pure water and a 10% (v/v) polyglycerol solution for Example 2.
Figure 25:
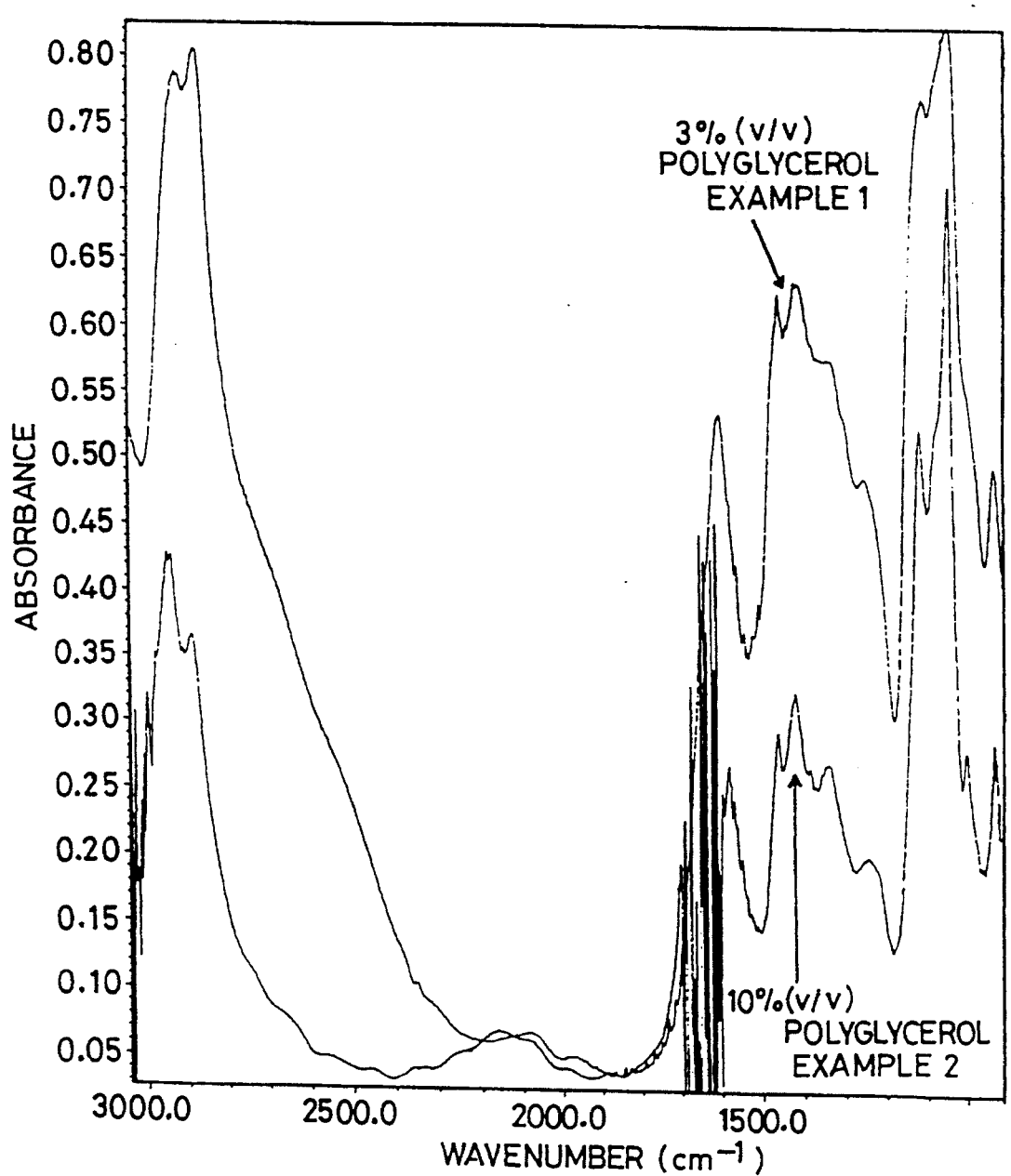
FIG. 25 shows spectrum of 10% (v/v) polyglycerol for Example 2 and spectrum of 3% (v/v) polyglycerol for Example 1.

FIG. 24 compares, on an equivalent absorbance scale, the transmission spectra of pure water and a solution containing 10% (v/v) of the polyglycerol additive and 90% (v/v) water (both spectra are ratioed with respect to an air background). FIG. 25 compares, on an equivalent absorbance scale, (i) the result of subtracting 90% of the water spectrum from the spectrum of the mixture containing 10% polyglycerol +90% water with (ii) the DRIFTS spectrum of a mixture containing 3% polyglycerol and 97% water. The comparison shows that the main absorbance bands due to polyglycerol in the DRIFTS and transmission spectra are well correlated. However, there are significant shifts in the frequency of C—H stretching and O—H bending vibrations in the liquid spectrum (transmission) as compared to the solid spectrum (DRIFTS). It is also notable that the transmission spectrum has sharper and more well defined peaks; this is particularly true for bands due to the ether group in the wavenumber region 1280–950 cm$^{-1}$.

Figure 26:
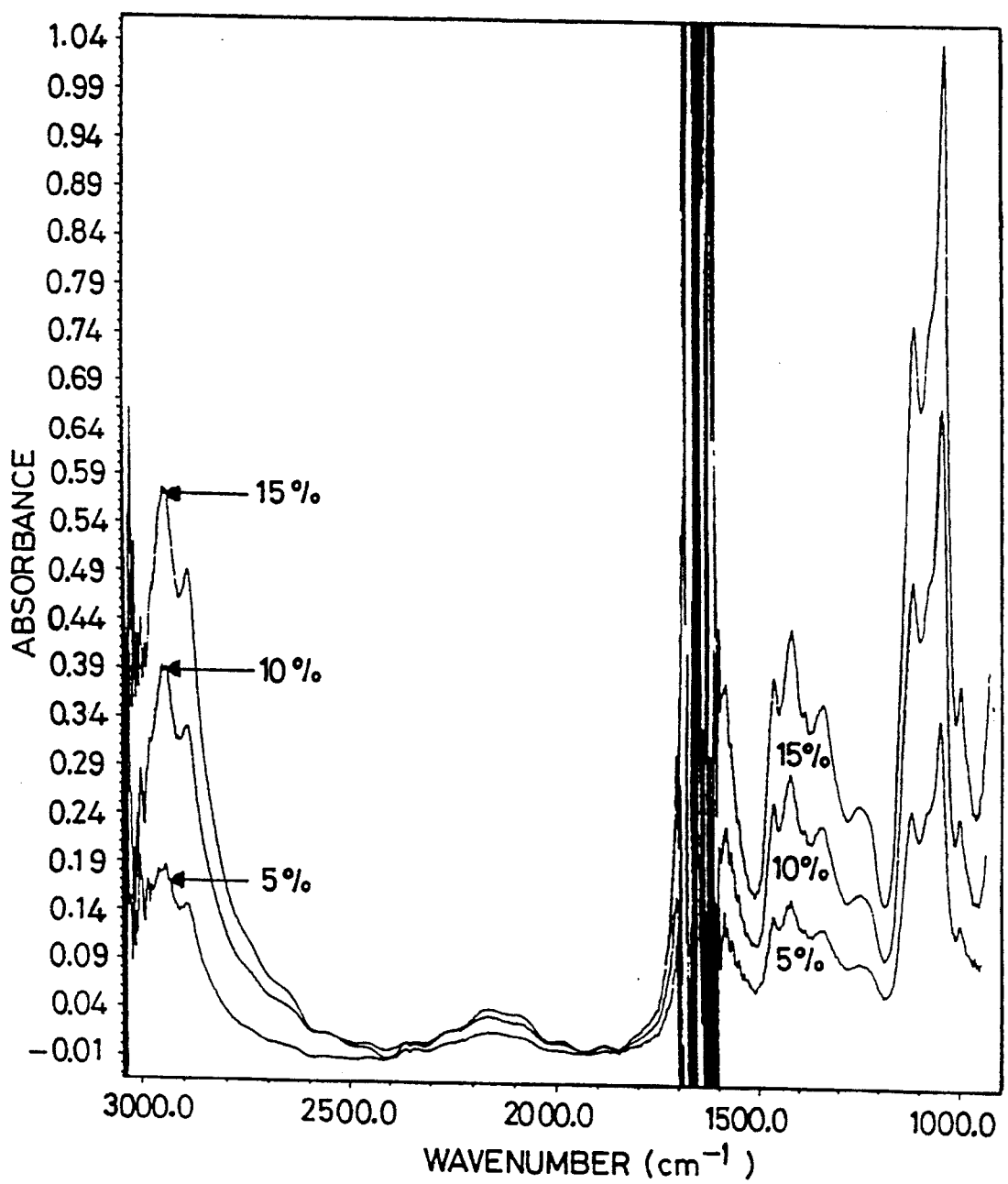
FIG. 26 shows spectra of 5, 10 and 15% (v/v) polyglycerol for Example 2.
Figure 27:
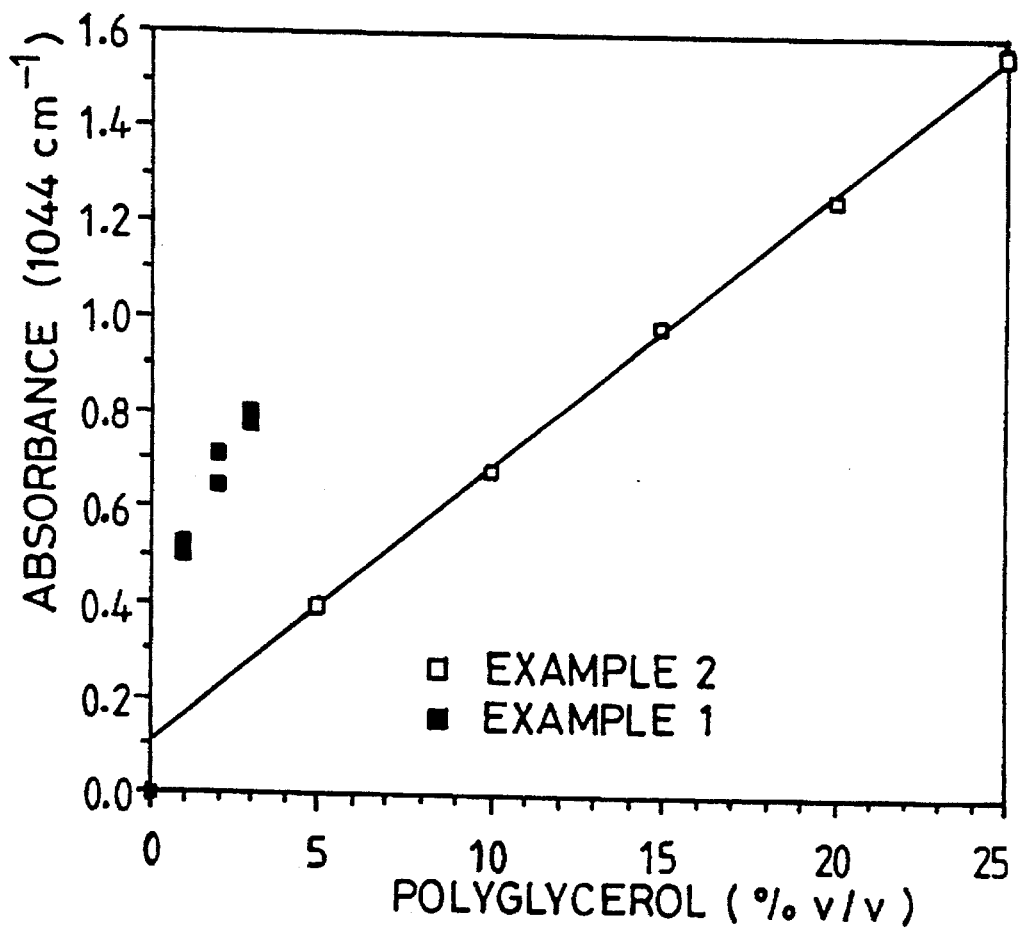
FIG. 27 shows peak height calibrations for polyglycerol product. 1044 cm$^{-1}$. It provides a comparison of Examples 1 and 2.

FIG. 26 shows the systematic increase in the absorbance of polyglycerol bands in transmission spectra as a function of polyglycerol concentration. FIG. 27 compares the linear relationship between peak height (ether group absorbance at 1044 cm$^{-1}$) and polyglycerol concentration given by transmission spectra with the non-linear relationship between equivalent parameters given by DRIFTS spectra.

Analysis of Results

Water-based drilling fluid formulations used in the field are complex, and their centrates will contain varying concentrations of several polymer/organic components as well as varying concentrations of inorganic salts. Thus, the application of the procedures described in Examples 1 and 2 to the quantitative analysis of such complex multicomponent centrates requires the use of multivariate calibration methods to deconvolve the contributions of each analyte component to the FTIR spectra of the mixtures. A number of multivariate calibration techniques can be used to build quantitative models for the infrared determination of several polymer/organic components in complex mixtures. These multivariate calibration techniques include principal component regression (PCR), partial least squares (PLS) path modelling, and artificial neural networks (ANN).

In developing methods for analysis of multicomponent centrates, 30 aqueous solutions containing varying concentrations of inhibitive polymer comprising a hydrophobic/hydrophyllic copolymer of ester (hydrophobic) and carboxylate (hydrophillic) comonomers (X) (0–8 g/l), xanthan gum (XC) (0–10 g/l), low viscosity carboxymethyl cellulose (CMC) (0–18 g/l) and KCl (0–5 wt. %) were prepared such that the concentration of each of the four components was varied independently with respect to the concentration of the other components. Each of the solutions was then analysed, in duplicate, using both procedures in Examples 1 and 2.

Figure 28A:
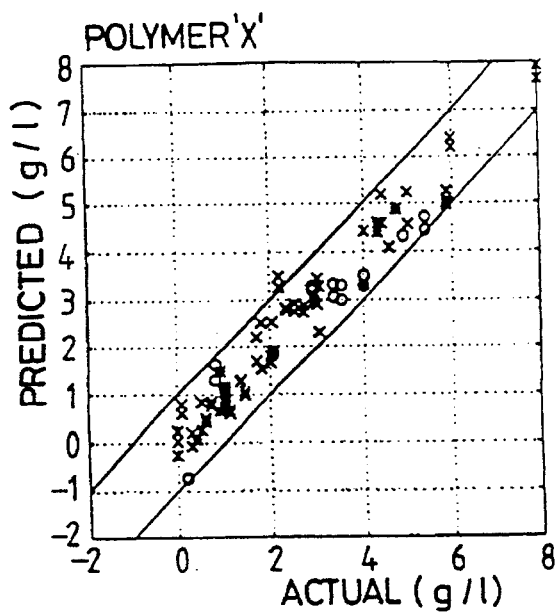
FIGS. 28A–28C show PLS model: correlations for X, XC and CMC respectively for Example 1.
Figure 28B:
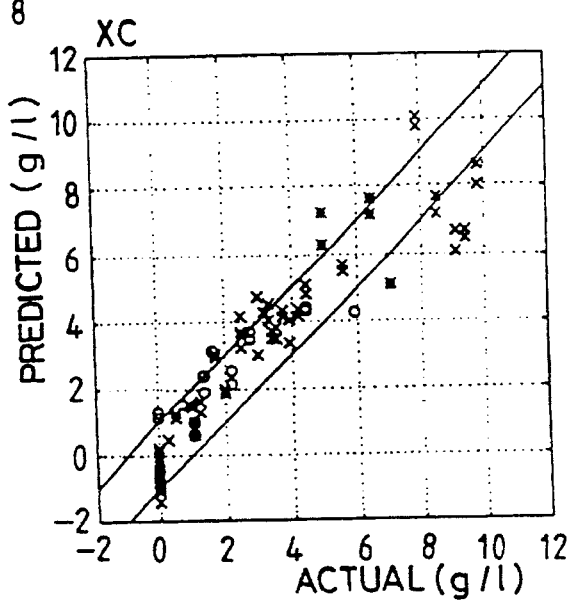
Figure 28C:
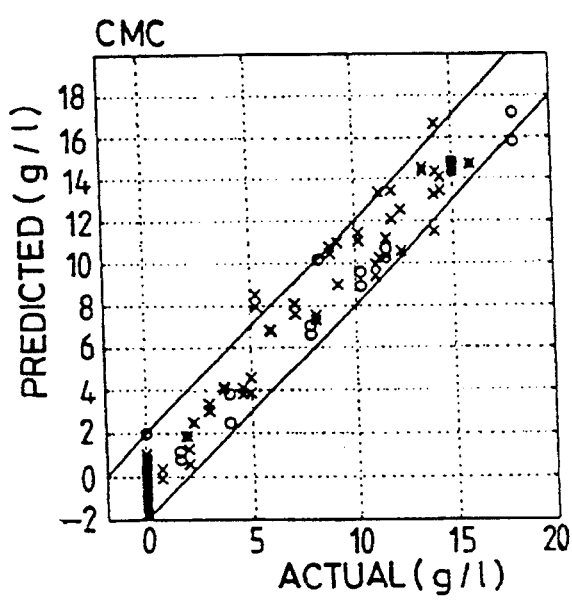

FIGS. 28A–C show FTIR predicted versus actual concentrations for each of the polymers given by a PLS model constructed using data from the raw spectra collected according to Example 1. The accuracy of the model is given by an evaluation of predictions obtained from truly independent test samples which are not used in constructing the model. Such an evaluation of the PLS model based on DRIFTS spectra indicates the levels of accuracy given below in Table 1 which also includes correlation coefficients for the calibration, validation and independent test samples.

TABLE 1

Analysis of multicomponent solutions using Example 1 (PLS model)

| Component | Accuracy | Calib (x) | Valid (o) | Indep (*) |
|---|---|---|---|---|
| X | within ±1.0 g/l | 0.975 | 0.959 | 0.948 |
| XC | within ±1.5 g/l | 0.932 | 0.878 | 0.927 |
| CMC | within ±2.0 g/l | 0.976 | 0.984 | 0.992 |

Figure 29A:
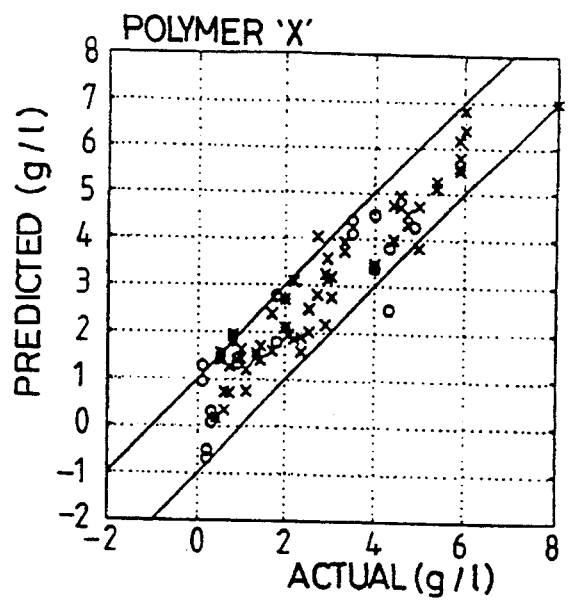
FIGS. 29A–29C show PLS model: correlations for X, XC and CMC respectively for Example 2.
Figure 29B:
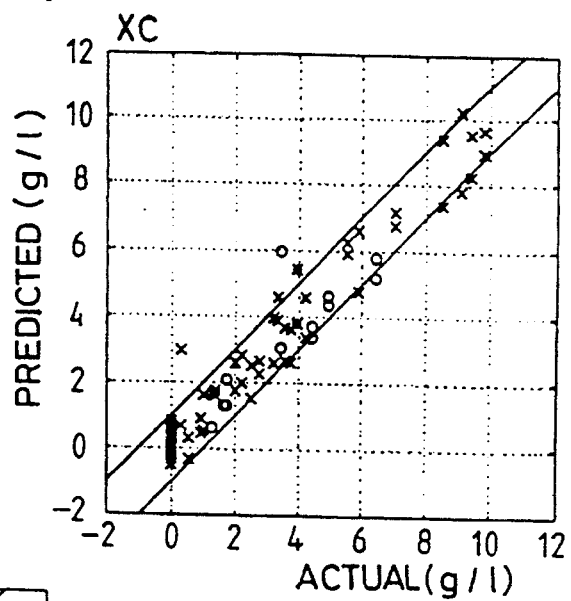
Figure 29C:
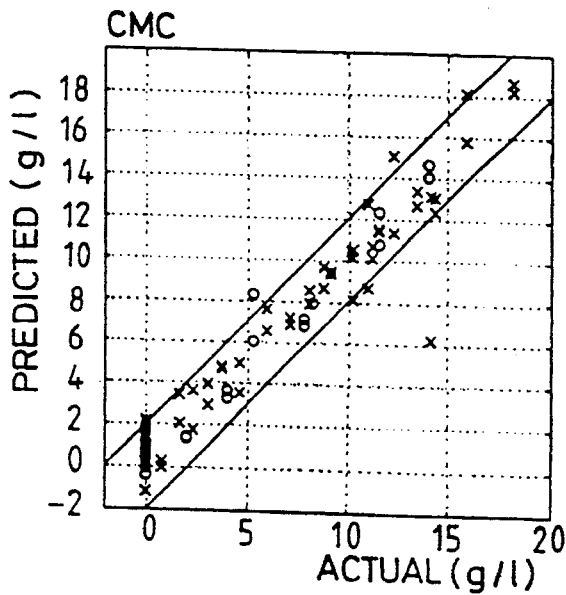

FIGS. 29A–C show predicted versus actual concentrations for each of the polymers given by a PLS model constructed using data from the spectra collected according to Example 2. An evaluation of the PLS model based on these spectra indicates the levels of accuracy given below in Table 2, which again also includes correlation coefficients for the calibration, validation and independent test samples.

TABLE 2

Analysis of multicomponent solutions using Example 2 (PLS model)

| Component | Accuracy | Calib (x) | Valid (o) | Indep (*) |
|---|---|---|---|---|
| X | within ±1.0 g/l | 0.977 | 0.906 | 0.764+ |
| XC | within ±1.5 g/l | 0.974 | 0.925 | 0.963 |
| CMC | within ±2.0 g/l | 0.963 | 0.979 | 0.983 |

A comparison of the correlations given in FIGS. 28 and 29 indicates that the Example 1 technique delivers less accurate determinations of XC in the concentration range 5–10 g/l, relative to those given by Example 2. This may be due to higher errors in pipetting 1 ml of the higher viscosity calibration standards during the collection of the spectra.

Application of Methods

Prior to field trials, the laboratory screening of novel inhibitive polymers for use in water-based drilling fluids involves an evaluation of their performance in terms of (i) their ability to stabilise the wellbore (in particular, stabilisation of reactive shale formations), and (ii) their ability to prevent the dispersion of drilled cuttings in order to optimise the removal of drilled solids from the circulating drilling fluid during drilling. In achieving the latter performance functions, the inhibitive polymer will be adsorbed on wellbore material and on solids removed by surface equipment. Thus, during drilling, the concentration of the polymer in the circulating drilling fluid will become depleted relative to its original concentration in the specified fluid formulation. The mud engineer will be required to maintain the concentration and, therefore, the performance, of the inhibitive polymer by adding extra polymer as drilling proceeds. Thus, in the economic evaluation of an inhibitive polymer, prior to field use, it is important to quantify depletion levels so that consumption rates can be anticipated. Depletion levels may be evaluated by controlled experiments to determine inhibitive polymer adsorption as a function of the concentration, mineralogy and surface area of drilled solids; the application of Example 1 and/or 2 allows the depletion levels of an inhibitive polymer to be quantified, both in the absence and in the presence of other polymers added to control fluid loss and rheology.

For example, in order to determine the depletion of inhibitive copolymer X on kaolinite and bentonite, several fluids, as detailed in Table 3, were prepared. The centrates of each fluid were analysed in duplicate using both the Example 1 and Example 2 PLS models described above.

TABLE 3

Composition of fluids designed to determine depletion of inhibitive copolymer X

| Series | X (g/l) | XC (g/l) | CMC (g/l) | Kaolinite (g/l) | Bentonite (g/l) |
|---|---|---|---|---|---|
| 1 | 4 | — | — | 10 to 100 | — |
| 2 | 4 | — | — | — | 10 to 100 |
| 3 | 4 | 4 | 10 | 10 to 100 | — |
| 4 | 4 | 4 | 10 | — | 10 to 10 |

Figure 30:
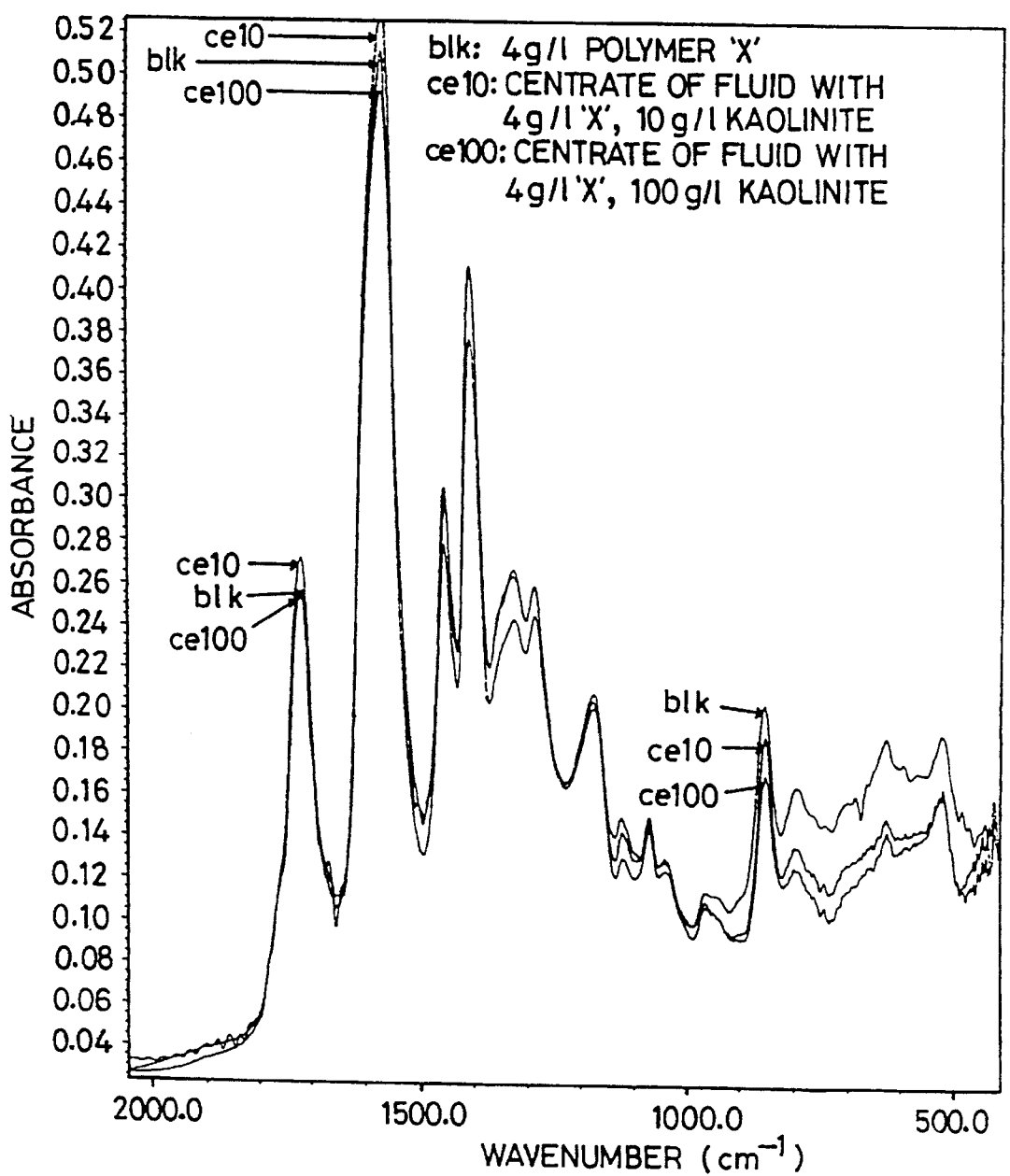
FIG. 30 shows spectra of 4 g/l polymer 'X' and fluids containing 4 g/l polymer 'X' and 10 and 100 g/l kaolinite for Example 1.
Figure 31:
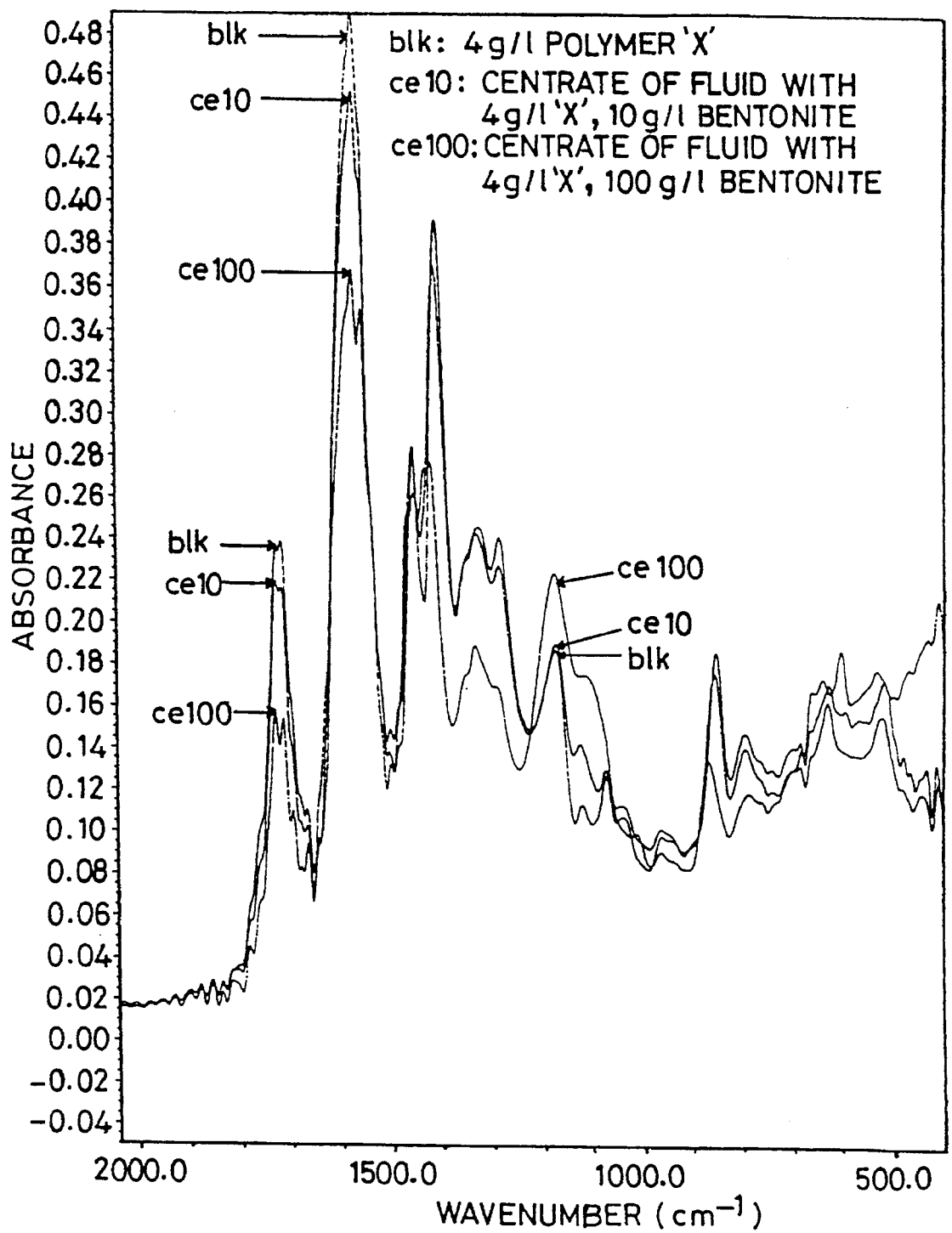
FIG. 31 shows spectra of 4 g/l polymer 'X' and fluids containing 4 g/l polymer 'X' and 10 and 100 g/l bentonite for Example 1.

DRIFTS spectra of centrates prepared from a selected number of the fluids in Series 1 and 2 are shown in FIGS. 30 and 31. The data shown in FIG. 30 indicate a realtively low level of adsorption of copolymer X on kaolinite. In contrast, appreciable quantities of the copolymer are adsorbed on bentonite, as indicated by the decreasing concentration of the copolymer in centrate as the bentonite content of the original fluid increases (FIG. 31).

Figure 32:
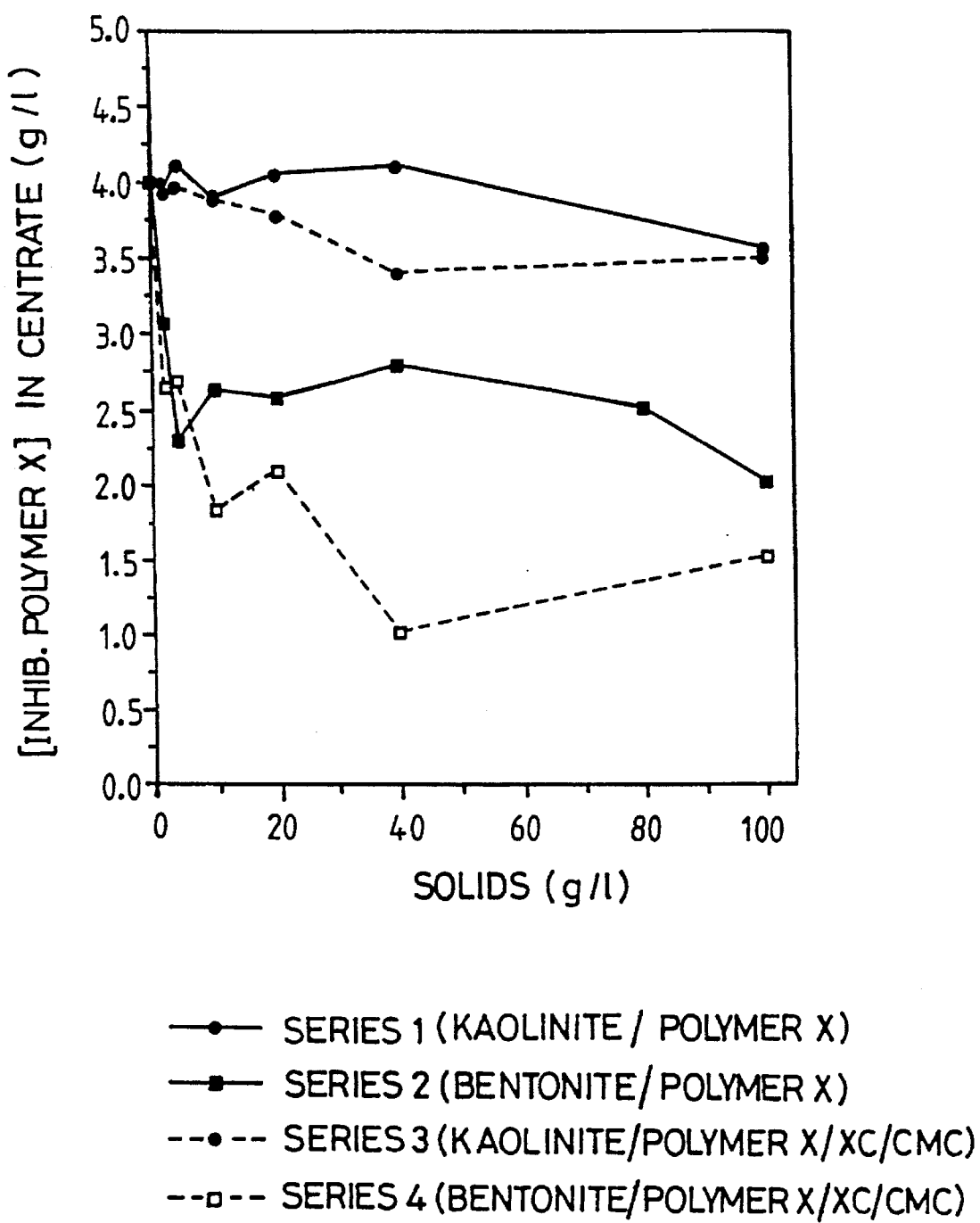
FIG. 32 shows adsorption of inhibitive polymer 'X' on kaolinite and bentonite (with and without XC and CMC). It plots [X] (g/l; Example 1) versus [solids] (g/l).

FIG. 32 compares quantitative analyses (Example 1) of copolymer X in centrates of the fluids in Series 1–4. The data indicate higher levels of polymer adsorption on bentonite relative to kaolinite; this is consistent with a comparison of the specific surface areas of the two minerals. Maximum levels of adsorption on bentonite (which occur as the solids content tends to zero) are around 600–700 mg/g (both in the absence and presence of XC and CMC), whilst those on kaolinite are around 10–20 mg/l. Although high levels of adsorption of the copolymer on bentonite are observed for highly dispersed suspensions of low solids content, the adsorption levels decrease to around 50–100 mg/g for more realistic suspensions which contain 20–100 g/l bentonite. The latter information is important in depletion calculations for field systems. It is also notable that significantly higher quantities of copolymer X are adsorbed onto both bentonite and kaolinite when XC and CMC are present and when the solids content is in the range 20–100 g/l; this indicates the importance of polymer-polymer interactions in the adsorption and depletion processes.

Figure 33B:
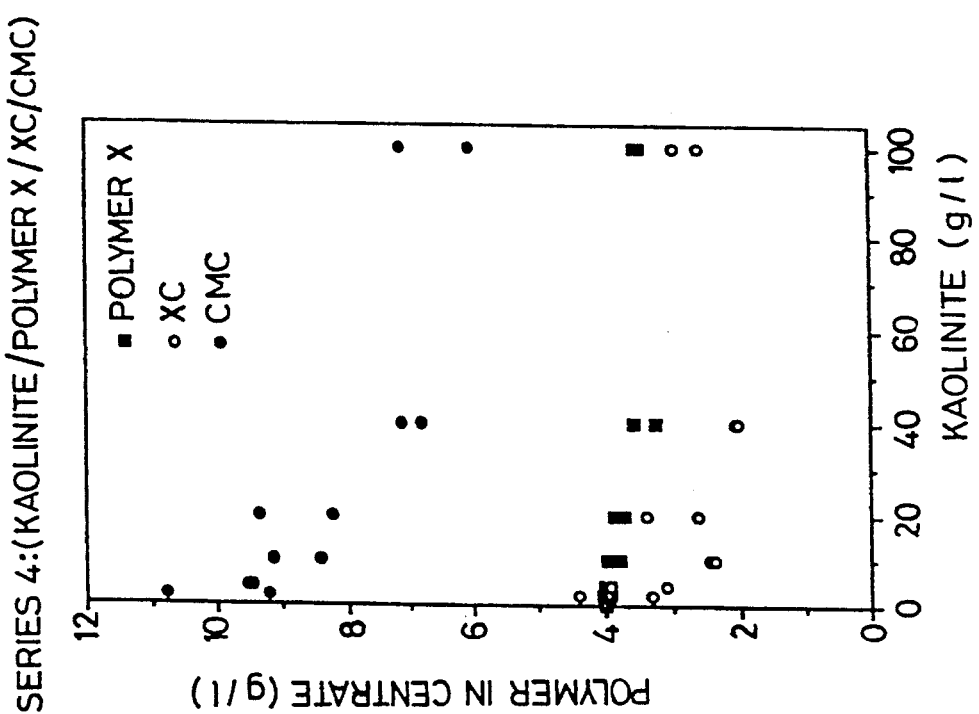
FIGS. 33A–33B show quantitative analyses (Example 1) of polymer 'X', XC and CMC in centrates of the fluids in Series 2 and 4 respectively.
Figure 33A:
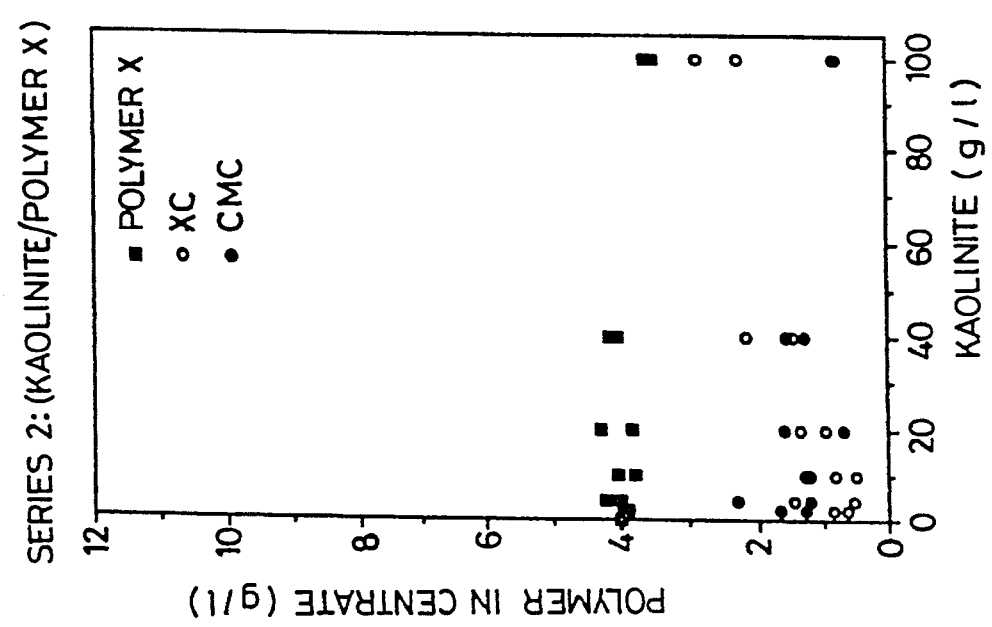

FIGS. 33A–B compare quantitative analyses (Example 1) of copolymer X, XC and CMC in centrates of the fluids in Series 2 and 4 respectively. Whilst the XC and CMC data for the Series 2 centrates indicate some degree of positive bias (all the data should be zero), it is important to note that these analyses relate to compositions which may not be sufficiently well represented in the calibration solutions. The data for the Series 4 centrates indicate higher levels of adsorption of XC and CMC on kaolinite relative to those of copolymer X; polymer-polymer interactions play an important role in the interpretation of these trends.

Figure 34:
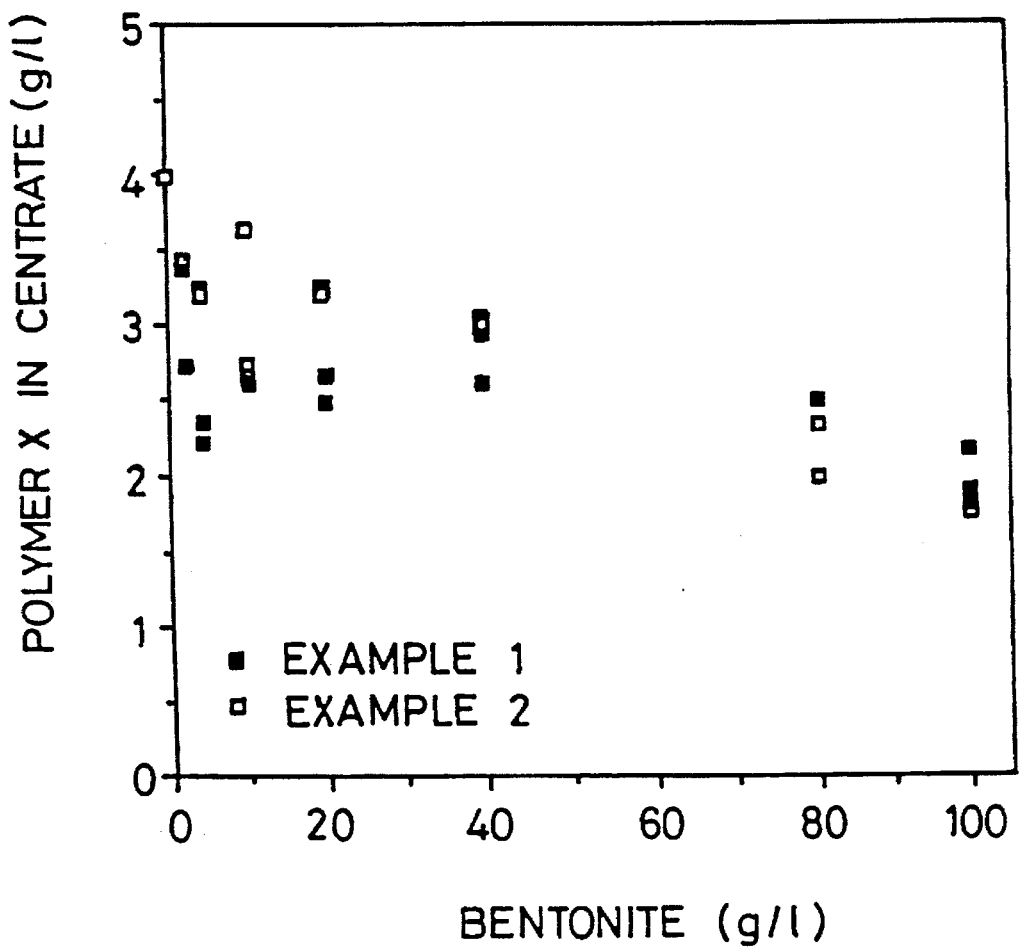
FIG. 34 shows adsorption of polymer 'X' on bentonite. It provides a comparison of the centrate analyses determined by Examples 1 and 2.

FIG. 34 compares Example 1 and Example 2 analyses of copolymer X in centrates of the fluids in Series 2; good agreement between analyses is indicated.

Figure 35:
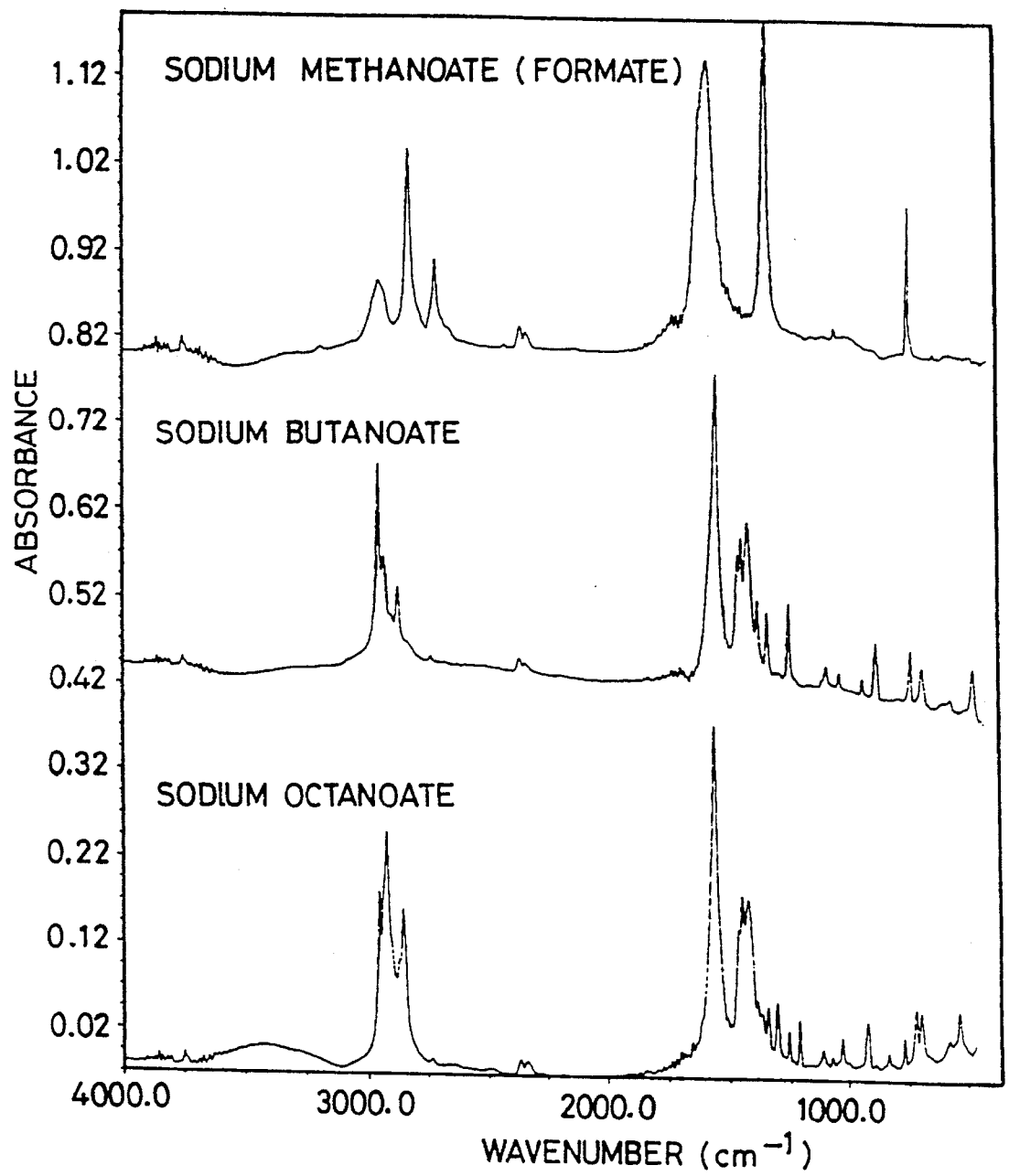
FIG. 35 shows spectra of 1 g/l solutions of sodium carboxylate salts for Example 1.
Figure 36:
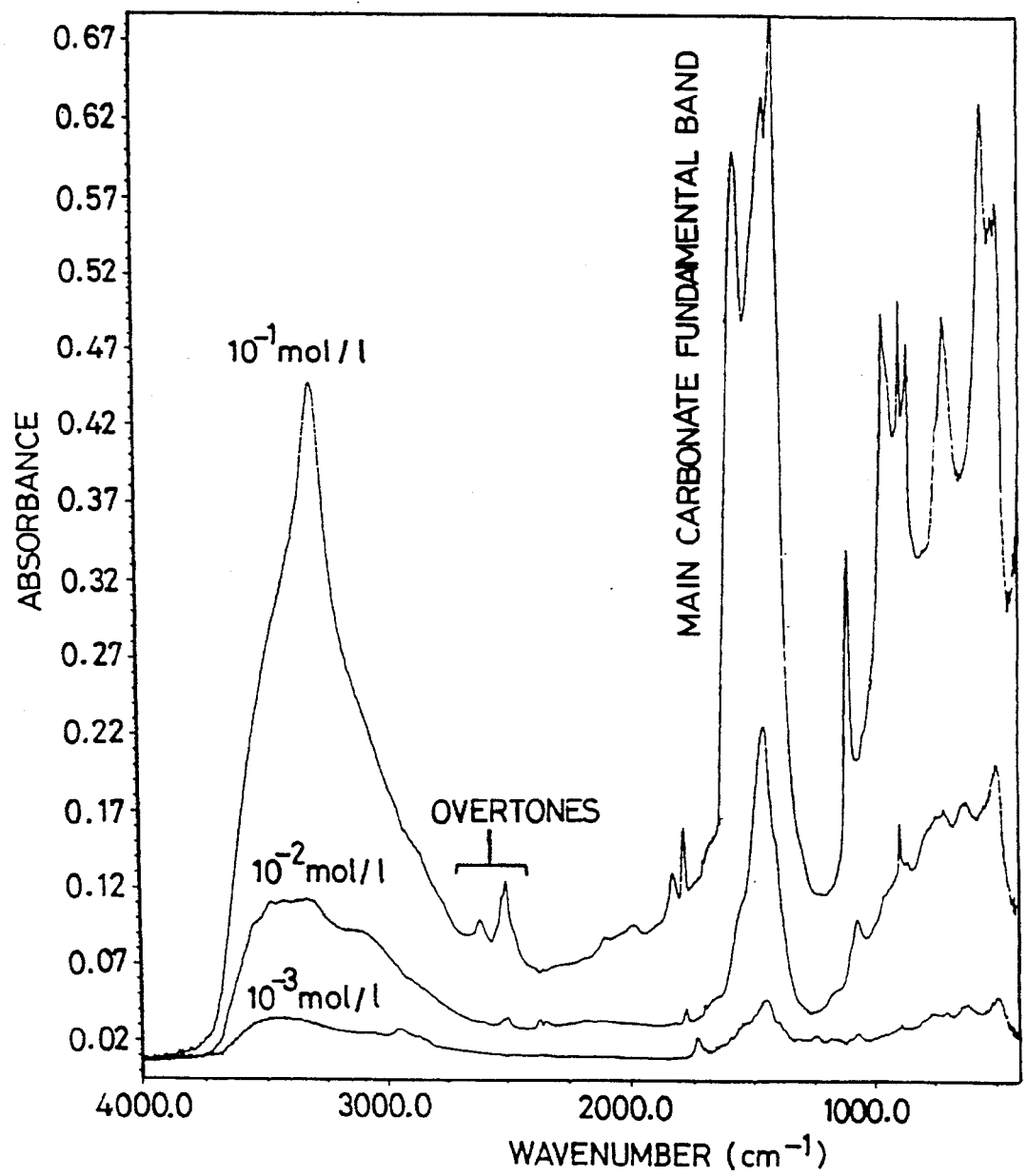
FIG. 36 shows determination of carbonate by Example 1.
Figure 37:
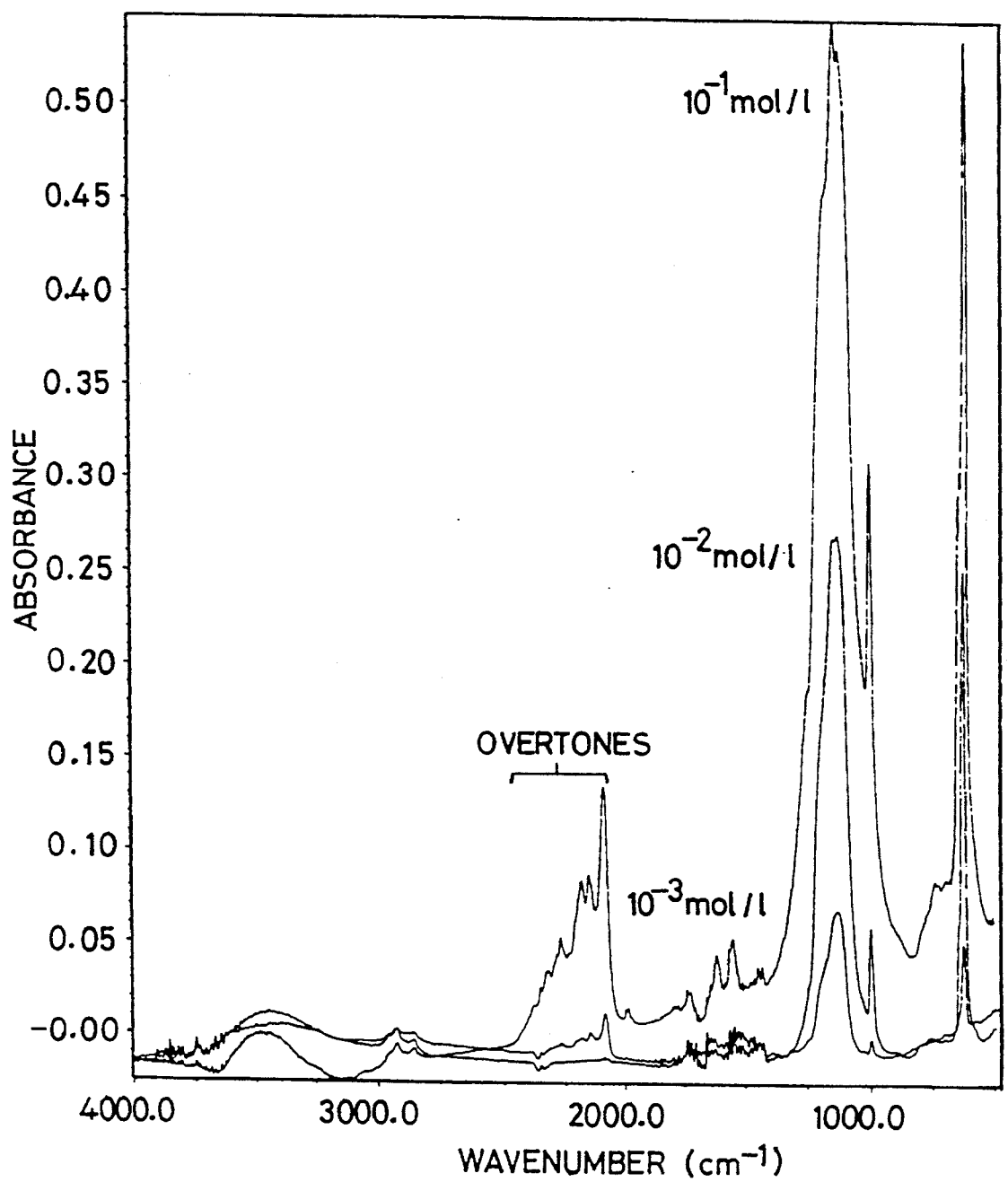
FIG. 37 shows determination of sulphate by Example 1.

DRIFTS may also be used to determine small organic anions and infrared active inorganic anions in centrates prepared from water-based drilling fluids. For example, FIG. 35 shows DRIFTS spectra of 1 g/l solutions of sodium methanoate (formate), sodium butanoate and sodium octanoate; the three carboxylate anions show characteristic features in the fingerprint and C—H stretching regions of the spectra. Both carbonate and sulphate anions can also be quantified by DRIFTS, as shown in FIGS. 36 and 37, respectively.

We claim:

1. A method of quantitative analysis of free organic components in a drilling fluid containing both solid and liquid components, the method comprising the steps of:

separating solid and liquid components of the drilling fluid using a non-filtering technique;

taking a sample of the liquid components;

mixing said sample with a solution of an inorganic carrier;

analyzing the resulting mixture using infrared spectroscopy so as to determine the amount of organic components in the mixture; and deriving the amount of free organic components in the drilling fluid from this analysis.

2. A method as claimed in claim 1, wherein the mixture is dried to leave a dried mixture of the organic components and the carrier, and the dried mixture is then analyzed using infrared spectroscopy.

3. A method as claimed in claim 2, wherein the dried sample/carrier mixture is crushed to a fine powder prior to analysis, and is analyzed using diffuse reflectance Fourier transform infrared spectroscopy.

4. A method as claimed in claim 2, wherein the carrier comprises KCl or KBr, and the carrier solution has a concentration of about 2M.

5. A method as claimed in claim 1, wherein the sample is analyzed as a liquid, using a direct transmission technique and Fourier transform infrared spectroscopy.

6. A method as claimed in claim 1, wherein the non-filtering separation technique is centrifugation.

7. A method as claimed in claim 1, wherein the liquid components are diluted prior to taking the sample.

* * * * *